United States Patent
Katase et al.

(10) Patent No.: US 9,974,318 B2
(45) Date of Patent: May 22, 2018

(54) METHOD FOR PRODUCING A LOW-LACTOSE MILK, MEDICINE, SUPPLEMENT, OR GALACTO-OLIGOSACCHARIDE

(71) Applicant: Amano Enzyme Inc., Nagoya-shi (JP)

(72) Inventors: Toru Katase, Kakamigahara (JP);
Yukiko Hoshi, Kakamigahara (JP);
Miho Nagaya, Kakamigahara (JP);
Shotaro Yamaguchi, Kakamigahara (JP); Masashi Minoda, Konan (JP);
Kazuhiro Nakanishi, Okayama (JP)

(73) Assignee: AMANO ENZYME INC., Nagoya-Shi (JP)

( * ) Notice: Subject to any disclaimer, the term of this patent is extended or adjusted under 35 U.S.C. 154(b) by 0 days. days.

(21) Appl. No.: 15/342,342

(22) Filed: Nov. 3, 2016

(65) Prior Publication Data

US 2017/0049120 A1    Feb. 23, 2017

Related U.S. Application Data

(62) Division of application No. 13/375,860, filed as application No. PCT/JP2010/057204 on Apr. 23, 2010, now Pat. No. 9,516,888.

(30) Foreign Application Priority Data

Jun. 5, 2009  (JP) ................. 2009-136735

(51) Int. Cl.
| C12P 21/02 | (2006.01) |
| A23C 9/12 | (2006.01) |
| C12N 9/38 | (2006.01) |
| A23L 33/17 | (2016.01) |
| A23L 33/21 | (2016.01) |
| A61K 38/00 | (2006.01) |

(52) U.S. Cl.
CPC ............. *A23C 9/1206* (2013.01); *A23L 33/17* (2016.08); *A23L 33/21* (2016.08); *C12N 9/2471* (2013.01); *C12Y 302/01023* (2013.01); *A23V 2002/00* (2013.01); *A61K 38/00* (2013.01)

(58) Field of Classification Search
None
See application file for complete search history.

(56) References Cited

U.S. PATENT DOCUMENTS

| 1,928,135 A * | 9/1933 | Peebles ................ A23C 1/04 |
| | | 159/4.07 |
| 2,174,734 A * | 10/1939 | Chuck ................ A23C 21/00 |
| | | 426/455 |
| 4,237,230 A | 12/1980 | Iida et al. |
| 6,699,703 B1 | 3/2004 | Doucette-Stamm et al. |
| 7,074,914 B1 | 7/2006 | Doucette-Stamm et al. |
| 8,354,259 B2 | 1/2013 | Hotchkiss et al. |
| 8,986,768 B2 * | 3/2015 | Tikanmaki ........... A23C 9/1206 |
| | | 426/491 |
| 9,516,888 B2 * | 12/2016 | Katase ................. A23C 9/1206 |

FOREIGN PATENT DOCUMENTS

| CN | 1737132 A | 2/2006 |
| CN | 101228904 A | 7/2008 |
| JP | 11-018763 A | 1/1999 |
| JP | 3886061 B2 | 2/2007 |
| WO | WO-2007/106407 A2 | 9/2007 |
| WO | WO-2009/009142 A2 | 1/2009 |

OTHER PUBLICATIONS

Choi et al. (Asian-Aust. J. Anim. Sci 20 (6) (2007) 989-993).*
Office Action for Korean Patent Application No. 10-2011-7030832, dated Nov. 21, 2016.
Zheng P, et al. Production of galacto-oligosaccharides by immobilized recombinant β-galactosidase from *Aspergillus candidus*. Biotechnol. J. 2006, 1, 1464-1470.
Z. Mozaffar et al., "Purification and Properties of β-Galactosidases from *Bacillus circulans*," Agric. Biol. Chem., 1984, 48(12), pp. 3053-3061.
A. Vetere et al., "Separation and characterization of three β-galactosidases from *Bacillus circulans*," Biochem. et Biophys. Acta., 1998, 1380, pp. 223-231.
Y. Ito et al., "Cloning and Characterization of the Gene Encoding a Novel β-Galactosidase from *Bacillus circulanst*," Biosci. Biotech. Biochem., 61(8), 1997, pp. 1270-1276.
H. Fujimoto et al., "Purification and properties of recombinant β-galactosidase from *Bacillus circulans*," Glycoconjugate Journal, 15, 1998, pp. 155-160.
H. Saito et al., "Preparation of Transforming Deoxyribonucleic Acid by Phenol Treatment," Biochim. Biophys. Acta, 72, 1963, pp. 619-629.
K. Nakanishi et al., "β-galactosidase no Ten'i Sayo o Riyo shita Kinosei Shokuhin no Seisan,"Annual Report 1990 of The Iijima Memorial Foundation for the Promotion of Food Science and Technology, 1990, pp. 227-232 and a cover page.
International Search Report dated Jun. 8, 2010, issued for PCT/JP2010/057204.
Supplementary European Search Report dated Oct. 16, 2012, issued for the corresponding European patent application No. 10783220.6.
Office Action dated Oct. 24, 2012, issued for the Chinese patent application No. 201080023941.7 and English abstract thereof.
Pakula and Sauer, "Genetic Analysis of Protein Stability and Function", Annu. Rev. Genet., 1989, 23: pp. 289-310.
Sanger, et al., "DNA sequencing with chain-terminating inhibitors", Proc. Natl. Acad. Sci. USA, Dec. 1977 vol. 74, No. 12, pp. 5463-5467.
Margulies, et al., "Genome Sequencing in Open Microfabricated High Density Picoliter Reactors", Nature. Sep. 15, 2005; 437(7057): 376-380.
Zhong, et al., "Protein sequencing by mass analysis of polypeptide ladders after controlled protein hydrolysis", Nature Biotechnology, vol. 22, No. 10, Oct. 2004. pp. 1291-1296.
Office Action dated May 19, 2014 in corresponding Russian Patent Application No. 2011150421.

* cited by examiner

*Primary Examiner* — Hope Robinson
(74) *Attorney, Agent, or Firm* — Locke Lord LLP; James E. Armstrong, IV; Nicholas R. Herrel

(57) ABSTRACT

Disclosed is a novel β-galactosidase. Specifically disclosed are a β-galactosidase derived from *Bacillus circulans* and a gene for the β-galactosidase. The β-galactosidase can be used, for example, in the production of milk, dairy products, fermented dairy products, galacto-oligosaccharides or supplements for foods.

13 Claims, 5 Drawing Sheets

METHOD FOR PRODUCING A LOW-LACTOSE MILK, MEDICINE, SUPPLEMENT, OR GALACTO-OLIGOSACCHARIDE

CROSS-REFERENCE TO RELATED APPLICATIONS

This application is a divisional application of U.S. application Ser. No. 13/375,860 filed Dec. 2, 2011, now U.S. Pat. No. 9,516,888, and which is the U.S. national phase, pursuant to 35 U.S.C. § 371, of PCT/JP2010/057204 filed Apr. 23, 2010, designating the United States and published in Japanese on Dec. 9, 2010 as publication WO 2010140435. PCT/JP2010/057204 claims priority to Japanese Patent Application Ser. No. 2009-136735, filed Jun. 5, 2009. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 2, 2011, is named AE09007Pamano_ST25.txt and is 68,988 bytes in size.

TECHNICAL FIELD

The present invention relates to a β-galactosidase. More particularly, the invention relates to a novel β-galactosidase isolated from *Bacillus circulans*, a gene thereof, and their use. For example, the β-galactosidase of the invention can be used in the production of low-lactose milks and galacto-oligosaccharides that are an intestinal *Bifidobacterium* growth factor, or can be used as an active ingredient for medicines or supplements in patients with lactose intolerance. The present application claims a priority date of Jun. 5, 2009 based on Japanese patent application No. 2009-136735, which is hereby incorporated by reference in its entirety.

BACKGROUND ART

Beta-galactosidase (EC3.2.1.23) is an enzyme that hydrolyzes the β-D-galactoside bond to release D-galactose, and, in general, it is widely distributed in microorganisms, and animals and plants. Beta-galactosidase is also referred to as lactase, and has been used as an enzyme for the production of a whey syrup from whey that is by-produced during the production of low-lactose milk for lactose intolerance or cheese, or as an active ingredient for medicines or supplements in patients with lactose intolerance. In addition, β-galactosidase has an ability to transfer the galactoside bond, and a method to prepare galacto-oligosaccharides (oligosaccharides with galactose residues) using this ability is known. Beta-galactosidases from a koji bacterium (*Aspergillus oryzae*), a yeast (*Kluyveromyces lactis, Kluyveromyces marxinus*), and a bacterium (*Bacillus circulans*) are known for use in these applications.

Among these, β-galactosidase derived from *Bacillus circulans* has been studied by Mozaffer et al. (non-patent document 1), Vetere et al. (non-patent document 2), and Ito et al. (non-patent documents 3 and 4). According to the non-patent document 1, purification of two kinds of enzymes each having a molecular weight of 240 kDa and 160 kDa is reported. It is further reported that the former has a high hydrolyzing activity, and the latter has a high transgalactosylation activity, and that the former showed a higher hydrolyzing activity against a synthetic substrate p-nitrophenyl-β-D-galactopyranoside (ONPG) than against lactose. On the other hand, according to the non-patent document 2, purification of three kinds of enzymes each having a molecular weight of 212 kDa, 145 kDa, and 86 kDa is reported. However, mutual protein chemical correlation and molecular biological characteristics (genetically) of these plural enzymes were not clear. In addition, in the non-patent documents 3 and 4, a gene cloning of the 67 kDa enzyme, and properties of the recombinant protein are reported, but the enzyme is specific to the β-1,3 bond, and does not act on the β-1,4 bond that is a bond of lactose present in a milk. Therefore, such an enzyme is different from the β-galactosidase ordinarily used in the treatment of milk or lactose derived from milk. In addition, two kinds of β-galactosidase genes derived from *Bacillus circulans* are registered at the GENBANK™ (GENBANK™ accession number of L03424 and L03425), but only gene sequences for these have been reported and it is not certain whether such genes encode actually an active protein.

PRIOR ART DOCUMENTS

Non-Patent Documents

Non-patent document 1: Mozaffar, Z., Nakanishi, K., Matsuno, R., and Kamikubo, T., Agric. Biol. Chem., 48(12), 3053-3061, 1984
Non-patent document 2: Vetere, A., and Paoletti, S. Biochem. Biophys. Acta., 1380, 223-231 (1998)
Non-patent document 3: Ito. Y., and Sasaki, T. Biosci. Biotech. Biochem., 61(8), 1270-1276 (1997)
Non-patent document 4: Fujimoto, H., Miyasato, M., Ito, Y., Sasaki, T., and Ajisaka, K. Glycoconjugate Journal, 15, 155-160 (1998)
Non-patent document 5: Saito, and Miura. Biochim. Biophys. Acta, 72, 619-629 (1963)

SUMMARY OF THE INVENTION

Problems to be Solved by the Invention

Thus, plural enzymes have been reported as β-galactosidase derived from *Bacillus circulans*, but there was a limitation in the production of enzyme preparations suitable for respective industrial applications including the production of low-lactose milks and galacto-oligosaccharides because mutual protein chemical correlation and molecular biological characteristics (genetically) of these plural enzymes were not clear.

Means for Solving Problem

The present invention provides a novel β-galactosidase derived from *Bacillus circulans*. The present inventors have found an enzyme (referred to as "β-Gal1" in the present specification) having a molecular weight of 195 kDa (as estimated by SDS-PAGE 189.3 kDa by mass spectrometry) which has not been reported so far, in the course of studies on β-galactosidases produced by *Bacillus circulans*, and have succeeded in cloning of the gene that encodes said enzyme (hereinafter referred to as the present gene). In addition, the base sequence of the present gene and the deduced amino acid sequence are greatly different from those of three kinds of β-galactosidases derived from *Bacil-*

*lus circulans* which have been reported so far (see the non-patent document 3 concerning the amino acid sequence, GENBANK™ accession No L03424 and L03425), and they were found to be novel. Moreover, the present inventors have found that *Bacillus circulans* produces three kinds of enzymes (hereinafter referred to as "β-Gal2", "β-Gal3", and "β-Gal4" in this specification) having a low hydrolyzing activity against a synthetic substrate 2-nitrophenyl β-D-galactopyranoside: ONPG, i.e. having a high transgalactosylation activity. Furthermore, it has also been found that these three kinds of β-galactosidases are produced from the present gene (a gene encoding β-Gal1). In addition, a method for producing a protein group of these β-galactosidases has been established by introducing the present gene and a fragment thereof into a suitable host.

The invention has been completed based on the above results. The invention is shown as follows.

[1] A β-galactosidase derived from *Bacillus circulans* having a molecular weight of 195 kDa (by SDS-PAGE).

[2] A β-galactosidase derived from *Bacillus circulans*, including a fragment of the β-galactosidase according to [1].

[3] A β-galactosidase including the amino acid sequence of SEQ ID NO: 7 or its fragment showing a β-galactosidase activity.

[4] The β-galactosidase according to [3], wherein the fragment includes a region from the N-terminal to WSIG-NEIY (SEQ ID NO: 18) of the amino acid sequence of SEQ ID NO: 7.

[5] The β-galactosidase according to [3], wherein the fragment includes the amino acid sequence of any one of SEQ ID NO: 8 to SEQ ID NO:10.

[6] The β-galactosidase according to [3], which is encoded by a DNA including the sequence of SEQ ID NO: 5.

[7] A β-galactosidase gene including any one of DNAs selected from the group consisting of the followings (a) to (e):
  (a) DNA encoding the amino acid sequence of SEQ ID NO: 6 or 7;
  (b) DNA including the sequence of SEQ ID NO: 5;
  (c) DNA that hybridizes to the complementary sequence of the sequence of SEQ ID NO: 5 under stringent conditions;
  (d) DNA that is a degenerate DNA sequence of the sequence of SEQ ID NO: 5; and
  (e) DNA encoding a protein having a sequence which includes substitution, deletion, insertion, addition or inversion in one or a plurality of bases when the sequence of SEQ ID NO: 5 is a reference sequence, and which has a β-galactosidase activity.

[8] The β-galactosidase gene according to [7], wherein the protein having a β-galactosidase activity includes the amino acid sequence of SEQ ID NO: 7 or its fragment, wherein changes in the amino acid sequence are occurred in less than 60%, preferably less than 45%, and further preferably less than 25%.

[9] The β-galactosidase gene according to [8], wherein the changes are a conservative amino acid substitution.

[10] A β-galactosidase, which is encoded by the β-galactosidase gene according to any one of [7] to [9].

[11] A recombinant vector including the β-galactosidase gene according to any one of [7] to [9].

[12] The recombinant vector according to [11], which is an expression vector.

[13] A transformant into which the β-galactosidase gene according to any one of [7] to [9] has been introduced.

[14] A transformant into which the recombinant vector according to [11] or [12] has been introduced.

[15] A transformant according to [13] or [14], which is a bacterial cell, a yeast cell or a fungal cell.

[16] A method for producing a β-galactosidase, including the following steps of:
  (1) culturing the transformant according to any one of [13] to [15] under conditions such that a protein encoded by the β-galactosidase gene is produced; and
  (2) collecting the produced protein.

[17] An enzyme preparation including as an active ingredient the β-galactosidase according to any one of [1] to [6] and [10].

[18] The enzyme preparation according to [17], wherein the active ingredient is one or more β-galactosidases selected from the group consisting of β-galactosidase including the amino acid sequence of SEQ ID NO: 7, β-galactosidase including the amino acid sequence of SEQ ID NO: 8, β-galactosidase including the amino acid sequence of SEQ ID NO: 9, and β-galactosidase including the amino acid sequence of SEQ ID NO: 10.

[19] Use of the β-galactosidase of any one of [1] to [6] and [10] or the enzyme preparation of [17] or [18] for the production of a product selected from the group consisting of a low-lactose milk, a galacto-oligosaccharide that is an intestinal *bifidobacterium* growth factor, and a medicine or supplement for patients with lactose intolerance.

[20] A low-lactose milk, a galacto-oligosaccharide that is an intestinal *bifidobacterium* growth factor, and a medicine or supplement for patients with lactose intolerance, which are obtained by use of the β-galactosidase of any one of [1] to [6] and [10] or the enzyme preparation of [17] or [18].

TERMS

Figure 1:
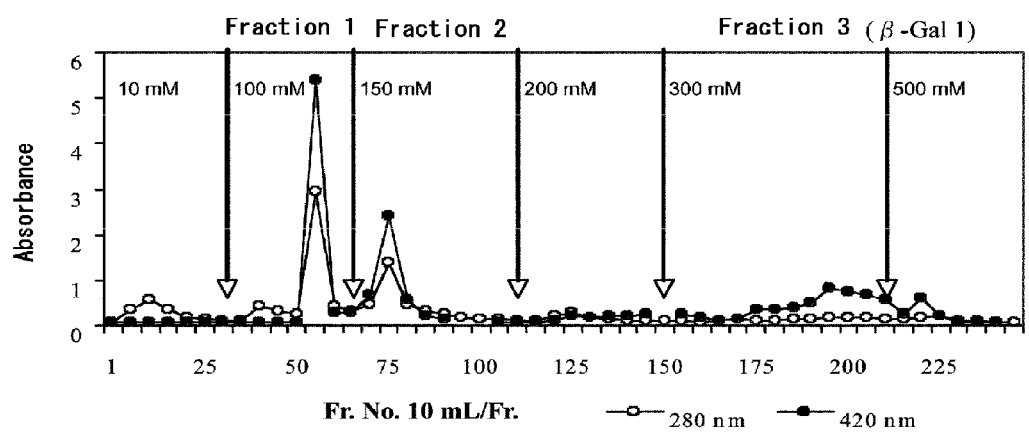
FIG. 1 is an elution pattern of a hydroxyapatite chromatography of a crude enzyme solution of β-galactosidase derived from *Bacillus circulans*. The absorbance at 280 nm corresponds to the protein and the absorbance at 420 nm measured by the ONPG method corresponds to the β-galactosidase activity, respectively.

The term "DNA encoding amino acid sequence" in the present invention denotes DNA from which the protein having the amino acid sequence is obtained when it is expressed, that is, DNA having a base sequence corresponding to an amino acid sequence of the protein. Therefore, the codon degeneracy is also taken into consideration.

In the present specification, the term "isolated" and "purified" are used interchangeably. The term "isolated" used with respect to the enzyme of the present invention (β-galactosidase), which is derived from a natural material, denotes a state in which components other than the enzyme are not substantially contained (in particular, contaminated protein is not substantially contained) in the natural material. Specifically, in the isolated enzyme of the present invention, the content of the contaminant protein is, for example, less than about 20%, preferably less than about 10%, further preferably less than about 5%, and yet further preferably less than about 1% with respect to the total amount on the weight basis. On the other hand, the term "isolated" when the enzyme of the present invention is prepared by genetically engineering technique denotes a state in which other components derived from a host cell to be used, a culture solution, and the like, are not substantially contained. Specifically, for example, in the isolated enzyme of the present invention, the content of the contaminant components is less than about 20%, preferably less than about 10%, further preferably less than about 5%, and yet further preferably less than about 1% with respect to the total amount on the weight basis. Unless otherwise specified, when merely the term "β-galactosidase" is used in this specification, it signifies the "β-galactosidase in an isolated state." The same is true to the term "the present enzyme" used instead of β-galactosidase.

The term "isolated" used with respect to DNA denotes typically that DNA is separated from other nucleic acid coexisting in nature when the DNA originally exists in nature. However, some of the other nucleic acid components such as a neighboring nucleic acid sequence in nature (for example, a sequence of a promoter region, a terminator sequence, or the like) may be included. For example, in the "isolated" state of the genome DNA, the isolated DNA preferably does not substantially include other DNA components coexisting in nature. On the other hand, in the "isolated" state of DNA prepared by a genetic engineering technique, for example, a cDNA molecule, and the like, preferably, the DNA does not substantially include cell components, a culture solution, or the like. Similarly, in the "isolated" state in the case of DNA prepared by chemical synthesis, the DNA does not include a precursor (a raw material) or chemical materials used in synthesis, for example, dNTP. Unless otherwise specified, when merely the term "DNA" is used in this specification, it signifies the "DNA in an isolated state."

In general, β-galactosidase shows a lactose hydrolyzing activity (an activity to hydrolyze lactose by the action on the β-1,4 bond) and a transgalactosylation activity (an activity to transfer galactose). Therefore the "β-galactosidase activity" in the invention is intended to include such two activities. The lactose hydrolyzing activity can be measured by the lactose method described in Examples. The other transgalactosylation activity can be expressed by using an index of the ratio of the activity value by the ONPG method shown in Examples/the activity value by the lactose method shown in Examples. It is known that the transgalactosylation activity becomes higher when the ratio of the activity value by the ONPG method shown in Examples/the activity value by the lactose method shown in Examples becomes smaller (non-patent document 1).

The "molecular weight" in the present invention means, unless otherwise indicated, a molecular weight measured by an SDS-PAGE (SDS-polyacrylamide gel electrophoresis).

(β-Galactosidase)

The first aspect of the invention provides a *Bacillus circulans*-derived β-galactosidase that has been successfully isolated and characterized by the present inventors. In one embodiment of the invention, the molecular weight of the β-galactosidase is 195 kDa (by SDS-PAGE). In the course of isolation and purification of the β-galactosidase, the present inventors have found that β-galactosidase (β-Gal2) with a molecular weight of 135 kDa, β-galactosidase (β-Gal3) of 86 kDa, and β-galactosidase (β-Gal4) of 160 kDa (each by SDS-PAGE) are produced, and also have found that these three kinds of β-galactosidases are all derived from one gene. On the other hand, it was confirmed that a gene in which a half or more of the C-terminal region was deleted expressed an active β-galactosidase. Based on these findings, another embodiment of the invention provides a β-galactosidase including a fragment (hereinafter referred to as the present fragment) of the above β-galactosidase (β-galactosidase with a molecular weight of 195 kDa, derived from *Bacillus circulans*). The length of the present fragment is not particularly limited as long as the present fragment shows a β-galactosidase activity, but it contains, for example, 5 to 98% protein, preferably 40 to 95% protein, and most preferably 55 to 75% protein relative to a standard protein. In addition, the present fragment preferably includes an N-terminal region of the standard protein. Specific examples of the present fragment are β-galactosidase (β-Gal2) having a molecular weight of 135 kDa, β-galactosidase (β-Gal3) having a molecular weight of 86 kDa, and β-galactosidase (β-Gal4) having a molecular weight of 160 kDa, all of which have been discovered by the present inventors.

The present fragment can also be obtained by a protease treatment. For example, the present fragment can be obtained by subjecting the purified β-galactosidase (β-galactosidase having a molecular weight of 195 kDa, derived from *Bacillus circulans*) to a protease treatment. Alternatively, the present fragment including the above β-galactosidase may be obtained by treating a culture solution of *Bacillus circulans* with a protease. There is no particular limitation to the protease used. For example, a commercially available protease preparation or an endogenous protease produced by *Bacillus circulans* can be used.

In one embodiment, the β-galactosidase of the invention includes the amino acid sequence of SEQ ID NO: 7. The amino acid sequence is formed by removing the signal peptide moiety from the amino acid sequence of SEQ ID NO: 6. In addition, the amino acid sequence of SEQ ID NO: 6 is an amino acid sequence that is deduced from the base sequence (SEQ ID NO: 5) of a gene obtained by cloning from *Bacillus circulans*. The β-galactosidase of the invention having the amino acid sequence of SEQ ID NO: 7 is a novel enzyme that is clearly different from three kinds of β-galactosidases derived from *Bacillus circulans* which have been reported so far, because of difference in the number of the amino acids and low homology (10 to 12%).

Other embodiment of the invention is a β-galactosidase including a fragment having the amino acid sequence of SEQ ID NO: 7. Herein, the fragment contains a region from the N-terminal to WSIGNEIY (SEQ ID NO: 18) of the amino acid sequence of SEQ ID NO: 7. The moiety sequence (WSIGNEIY SEQ ID NO: 18) is a putative active domain. A specific example of the fragment can include those having an amino acid sequence of any one of SEQ ID NO: 8 to SEQ ID NO: 10. The amino acid sequence of SEQ ID NO: 8 corresponds to Gal2, the amino acid sequence of SEQ ID NO: 9 corresponds to Gal3, and the amino acid sequence of SEQ ID NO: 10 corresponds to Gal4.

Generally, when a part of an amino acid sequence of a certain protein is modified, the modified protein may have the equal function to that of the protein before the modification. That is to say, the modification of the amino acid sequence may not have a substantial effect on the function of the protein, so that the function of the protein may be maintained before and after the modification. When this technical common sense is considered, an enzyme that has a recognizable slight difference in the amino acid sequence and has no substantially recognizable difference in the function as β-galactosidase can be regarded as an enzyme that is substantially the same as the above β-galactosidase in comparison with β-galactosidase (including any one of the amino acid sequences of SEQ ID NO: 7 to SEQ ID NO: 10) of the invention. The term "slight difference in the amino acid sequence" as used herein typically means that the amino acid sequence is mutated (changed) by the deletion or substitution of one to several amino acids (the upper limit: e.g. 3, 5, 7, or 10 amino acids) constituting the amino acid sequence, or by the addition, insertion, or combination thereof, of one to several amino acids (the upper limit: e.g. 3, 5, 7, or 10 amino acids). The identity (%) of between the amino acid sequence in the "substantially the same enzyme" and the amino acid sequence of the above β-galactosidase as a standard is preferably 90% or more, more preferably 95% or more, yet more preferably 98% or more, and most preferably 99% or more. In addition, the difference in the amino acid sequence may occur in a plurality of positions.

The "slight difference in the amino acid sequences" is preferably generated by a conservative amino acid substitution. Herein, the "conservative amino acid substitution" is a substitution in which the amino acid residue is substituted with an amino acid residue having a side chain with similar feature. The amino acid residues are divided into some families depending on side chains thereof, including basic side chains (e g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). The conservative amino acid substitution is preferably a substitution between amino acid residues of the same family.

The identity (%) between two amino acid sequences can be determined by the following procedure. Firstly, two sequences are aligned for optimum comparison of the two sequences (for example, a gap may be introduced into the first sequence so as to optimize the alignment with respect to the second sequence). When a molecule (amino acid residue) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an amino acid sequence equivalent to the polypeptide molecule of the present invention, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see the World Wide Web (www) at ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, FRANCE) or ISREC server. When the ALIGN program is used for comparison of the amino acid sequences, for example, PAM120 weight residue table can be used in which a gap length penalty is 12 and a gap penalty is 4. The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4.

(β-Galactosidase Gene)

The second aspect of the invention relates to a β-galactosidase gene. In one embodiment, the gene of the invention includes a DNA that encodes the amino acid sequence of SEQ ID NO: 6 or 7. A specific example of the embodiment is a DNA including the base sequence of SEQ ID NO: 5.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the base sequence set forth in SEQ ID NO: 5 and having the β-galactosidase activity (hereinafter, which is also referred to as "equivalent DNA"). The "equivalent base sequence" herein denotes a base sequence which is partly different from the base sequence set forth in SEQ ID NO: 6 but in which the function (herein, β-galactosidase activity) of the protein encoded by the sequence is not substantially affected by the difference.

A specific example of the equivalent DNA includes DNA that hybridizes to the complementary base sequence of the base sequence of SEQ ID NO: 5 under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5×Denhardt's solution, 1% SDS, 10% dextran sulfate, 10 µg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15 M NaCl, 15 mM sodium citrate, pH 7.0), 1×Denhardt's solution, 1% SDS, 10% dextran sulfate, 10 µg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality of bases (preferably one to several bases) when the base sequence of SEQ ID NO: 5 is a reference base sequence, and which has a β-galactosidase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA. The above-mentioned equivalent DNA can be obtained by modifying DNA having the base sequence shown in SEQ ID NO: 5 so as to include substitution, deletion, insertion, addition and/or inversion of base by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray.

A further example of the equivalent DNA can include DNA having difference in base as mentioned above due to polymorphism represented by SNP (single nucleotide polymorphism).

Herein as shown in the examples mentioned below, the proteins (Gal2, Gal3 and Gal4) including the amino acid sequences of SEQ ID NO: 8 to SEQ ID NO: 10 that were each a fragment of the amino acid sequence (Gal1) of SEQ ID NO: 7 showed a high β-galactosidase activity. One embodiment of the invention based on this fact provides a β-galactosidase gene that encodes a protein including the amino acid sequence set forth in SEQ ID No. 7, or a fragment thereof, wherein changes of less than 60%, preferably less than 45%, and more preferably less than 25% are occurred in the amino acid sequence.

The gene of the present invention can be prepared in an isolated state by using a standard genetic engineering technique, a molecular biological technique, a biochemical technique, and the like, with reference to sequence information disclosed in the present specification or attached sequence list. Specifically, the gene of the present invention can be prepared by appropriately using oligonucleotide probe/ primer capable of specifically hybridizing to the gene of the present invention from an appropriate genome DNA library or a cDNA library of *Bacillus circulans*, or cell body extract of *Bacillus circulans*. An oligonucleotide probe/primer can be easily synthesized by using, for example, a commercially available automated DNA synthesizer. As to a production method of libraries used for preparing the gene of the present invention, see, for example, Molecular Cloning, Third Edition, Cold Spring Harbor Laboratory Press, New York.

For example, a gene having the base sequence set forth in SEQ ID NO: 5 can be isolated by using a hybridization method using all or a part of the base sequence or its complimentary sequence as a probe. Furthermore, amplification and isolation can be carried out by using a nucleic acid amplification reaction (for example, PCR) using a synthesized oligonucleotide primer designed to specifically hybridize to a part of the base sequence. Furthermore, it is possible to obtain a target gene by chemical synthesis based on the information of the amino acid sequence set forth in SEQ ID NO: 6 or the base sequence set forth in SEQ ID NO: 5 (see, reference document: Gene, 60(1), 115-127 (1987)).

(Recombinant Vector)

Another aspect of the present invention relates to a recombinant vector containing the β-galactosidase gene of the present invention. The term "vector" as used in this specification is intended to refer to a nucleic acid molecule capable of transporting nucleic acid that is inserted in the vector to the inside of the target such as cells. The types or forms of vector are not particularly limited. Therefore, examples of the vector may be in a form of a plasmid vector, a cosmid vector, a phage vector, a viral vector (e.g., an adenovirus vector, an adeno-associated virus vector, a retrovirus vector, a herpes virus vector, etc).

According to the purpose of use (cloning, protein expression), and by considering the types of host cells, an appropriate vector is selected. Specific examples of the vector include a vector using *Escherichia coli* as a host (M13 phage or the modified body thereof, λ phage or the modified body thereof, pBR322 or the modified body thereof (pB325, pAT153, pUC8, etc.) and the like), a vector using yeast as a host (pYepSec 1, pMFa, pYES2, etc.), a vector using insect cells as a host (pAc, pVL, etc.), a vector using mammalian cells as a host (pCDM8, pMT2PC, etc.), and the like.

The recombinant vector of the present invention is preferably an expression vector. The term "expression vector" is a vector capable of introducing the nucleic acid inserted therein into the target cells (host cells) and being expressed in the cells. The expression vector usually includes a promoter sequence necessary for expression of the inserted nucleic acid and an enhancer sequence for promoting the expression, and the like. An expression vector including a selection marker can be used. When such an expression vector is used, by using the selection marker, the presence or absence of the introduction of an expression vector (and the degree thereof) can be confirmed.

Insertion of the gene of the present invention into a vector, insertion of the selection marker gene (if necessary), and insertion of a promoter (if necessary), and the like, can be carried out by a standard recombination DNA technology (see, for example, Molecular Cloning, Third Edition, 1.84, Cold Spring Harbor Laboratory Press, New York, a already-known method using restriction enzyme and DNA ligase).

(Transformant)

The present invention further relates to a transformant into which the gene of the present invention is introduced. In the transformant of the preset invention, the gene of the present invention exists as an exogenous molecule. Preferably, the transformant of the present invention can be preferably prepared by transfection or transformation using the vector of the present invention mentioned above. The transfection and transformation can be carried out by, for example, a calcium phosphate coprecipitation method, electroporation (Potter, H. et al., Proc. Natl. Acad. Sci. U.S.A. 81, 7161-7165(1984)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast-polyethylene glycol method (Yelton, M. M. et al., Proc. Natl. Acad. Sci. 81, 1470-1474 (1984)), and the like.

The host cell is not particularly limited as long as the β-galactosidase of the invention can be expressed, and it can be selected from, for example, *Bacillus* genus bacteria (e.g., *Bacillus subtillus, Bacillus likemiformis, Bacillus circulans*, etc.), lactic acid bacteria (e.g., *Lactococcus, Lactobacillus, Streptococcus, Leuconostoc, Bifidobacterium*, etc.), other bacteria (e.g. *Escherichia, Streptomyces*, etc.), yeast (e.g., *Saccharomyces, Kluyveromyces, Candida, Torula, Torulopsis*, etc.), and filamentous fungi (Eumycetes) (e.g., *Aspergillus* genus fungi such as *Aspergillus oryzae* and *Aspergillus niger, Penicillium* genus fungi, *Trichoderma* genus fungi, *Fusarium* genus fungi, etc.).

(Production of β-Galactosidase)

A further aspect of the invention is to provide a method for producing a β-galactosidase. In one embodiment of the production method of the invention, the β-galactosidase is produced by using the above-mentioned transformant. In the production method in this embodiment, the transformant is cultured under the conditions such that a protein encoded by a gene introduced therein is produced (step (1)). The culture conditions of transformant are known as to various vector-host systems, and a person skilled in the art can easily set an appropriate culture condition.

Culture methods and culture conditions are not particularly limited as long as the intended protein β-galactosidase can be produced. That is to say, methods and culture conditions suitable for culturing microorganisms to be used can be appropriately set to the conditions such that the β-galactosidase is produced. Liquid culture or solid culture may be employed as a culture method, but liquid culture is preferably used. The culture condition will be described with reference to a liquid culture as an example.

As the medium, any medium can be used as long as transformants to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used. In order to promote the growth of transformants to be used, vitamin, amino acid, and the like, may be added to the medium. The medium is cultured under the aerobic conditions such that the pH of the medium is adjusted to, for example, about 3 to 10 (preferably about 7 to 8), and the culture temperature is generally about 10° C. to 50° C. (preferably about 20° C. to 37° C.) for 1 to 7 days (preferably 3 to 4 days). An example of the culture method may include a shake culture method, and an aerobic submerged culture method by using a jar fermenter.

The produced protein (β-galactosidase) following the culturing step is collected (step (2)). When β-galactosidase is collected from the culture solution, the enzyme can be obtained by separation and purification by removing insoluble matters by, for example, filtration of culture supernatant, centrifugation, and the like, followed by carrying out an appropriate combination of concentration by ultrafiltration membrane, salting out by ammonium sulfate precipitation, dialysis, various types of chromatography of an ion-exchange resin, and the like. On the other hand, when β-galactosidase is collected from cell bodies, the target protein can be obtained by pulverizing the cell bodies by pressuring treatment, ultrasonic treatment, or the like, followed by separation and purification thereof similar to the above. After collection of the cell bodies from a culture solution by filtration, centrifugation, etc., a series of processes (pulverizing, separation, and purification of cell bodies) mentioned above may be carried out.

The purification degree of β-galactosidase is not particularly limited. Furthermore, the final form of the β-galactosidase may be a liquid state or a solid state (including a powdery state).

(Enzyme Preparation)

β-galactosidase of the present invention is provided in a form of, for example, an enzyme preparation. The enzyme preparation may contain, in addition to an active ingredient (β-galactosidase of the present invention), excipient, buffer agents, suspension agents, stabilizer, preservatives, antiseptics, physiologic saline, and the like. Examples of the excipient may include lactose, sorbitol, D-mannitol, sucrose, and the like. Examples of the buffer agent may include phosphate, citrate, acetate, and the like. Examples of the stabilizer may include propylene glycol, and ascorbic acid, and the like. Examples of the preservative may include phenol, benzalkonium chloride, benzyl alcohol, chlorobutanol, methyl paraben, and the like. Examples of the antiseptic may include benzalkonium chloride, parahydroxybenzoate, chlorobutanol, and the like.

In one embodiment of the enzyme preparations of the invention, one or more β-galactosidases as an active ingredient selected from the group consisting of a β-galactosidase including the amino acid sequence of SEQ ID NO: 7, a β-galactosidase including the amino acid sequence of SEQ ID NO: 8, a β-galactosidase including the amino acid sequence of SEQ ID NO: 9, and a β-galactosidase including the amino acid sequence of SEQ ID NO: 10 are used. In one embodiment, an enzyme preparation containing all these four kinds of β-galactosidases is provided.

(Use of β-Galactosidase)

A further aspect of the invention provides use of the β-galactosidase or enzyme preparation of the invention. Examples of such use are a production of a low-lactose milk, a production of a galacto-oligosaccharide which is an intestinal *bifidobacterium* growth factor, or a production of a medicine or supplement for patients with lactose intolerance. Lactose in raw materials can be reduced by using the β-galactosidase or enzyme preparation of the invention. For example, the low-lactose milk can be obtained by adding β-galactosidase of 1 U to a raw milk of 1 mL, and allowing the mixture at a low temperature of 10° C. so that the lactose is hydrolyzed. In the production of the galacto-oligosaccharide, β-galactosidase of 100 LU is added to a 40% lactose solution (pH 7.0) which has been dissolved by preheating and allowed to stand at 40° C. for 5 hours, thereby to produce the galacto-oligosaccharide, for example. Further, the galacto-oligosaccharide is represented by Gal-(Gal)n-

Glc (n is usually 0 to 3) (Gal: galactose residue, Glc: glucose residue). The bond mode includes α1-3, and α1-6 other than β1-6, β1-3, β1-4, and β1-2.

EXAMPLES

1. Purification of β-Galactosidase Derived from *Bacillus circulans*

(a) Measurement of β-Galactosidase Activity

In the following purification, a measurement of β-galactosidase activity was carried out by two kinds of methods such as (i) a method where 2-nitrophenyl-β-D-galactopyranoside (ONPG) was used as a substrate and (ii) a method where lactose was used as a substrate. Both methods were performed according to the method described in a non-patent document 1. In addition, the protein concentration was represented in terms of the absorbance at 280 nm.

i) ONPG Method

A 100 mM phosphate buffer solution (pH 6.0) 1.98 ml containing 0.245% ONPG was prewarmed at 40° C. for 10 minutes. After addition of a sample 20 μl to the buffer solution, the mixture was reacted at 40° C. for 10 minutes, and a 10% sodium carbonate solution 2.0 ml was added to stop the reaction. The absorbance of the reaction solution was measured at 420 nm, and β-galactosidase activity was calculated based on an activity of producing 1 μmol of 2-nitrophenol per one minute as 1 U.

ii) The Lactose Method

A 100 mM phosphate buffer solution (pH 6.0) 2 ml containing 5% lactose was prewarmed at 40° C. for 10 minutes. After addition of a sample 50 μl to the buffer solution, the mixture was reacted at 40° C. for 15 minutes, and boiled in a boiling bath to stop the reaction. Glucose concentration for the reaction solution of 100 μl was measured by the Glucostat method. That is, a 0.1N sodium hydroxide solution 100 μl was added to the reaction solution 100 μl, and the mixture was allowed to stand for one minute, and then 0.1N acetic acid and an acetate buffer solution (pH 5.0) 3 ml were added. To the solution was added a Glucostat solution (Ono Pharmaceutical Co., Ltd., Osaka, JAPAN) of 500 μl, and the increase rate of the absorbance at 550 nm was measured to calculate the lactose hydrolyzing activity when an activity of producing 1 μmol of glucose per one minute was defined as 1 U.

(b) Preparation of Crude Enzyme Powder of β-Galactosidase

*Bacillus circulans* ATCC 31382 was inoculated into a liquid culture medium containing 3.0% soy bean peptone, 2.5% meat extract, 1.0% yeast extract, and 0.5% lactose, and cultured under shaking at 30° C. for 3 days. After removal of the cell bodies by centrifuge, the resulting culture supernatant was treated with an ultrafiltration membrane (AIP-1013D, manufactured by Asahi Kasei Corporation, Tokyo, JAPAN) to obtain a 5-fold concentrate solution. The obtained concentrate was spray-dried to obtain a crude β-galactosidase enzyme powder.

(c) Purification of β-Galactosidase

A solution 50 ml obtained by dissolving the resulting crude enzyme powder in a 10 mM sodium phosphate buffer solution (pH 6.0) to a concentration of 5.0% was charged to a hydroxyapatite gel column (CHT™ Ceramic hydroxyapatite, manufactured by BIO-RAD Laboratories, Inc., Waltham, Mass., USA; 2.5 cm in inside diameter, 25 cm in length) which had been equilibrated with the same buffer solution, and unadsorbed proteins were eluted with a 10 mM sodium phosphate buffer solution (pH 6.0). After that, the enzyme was eluted by the stepwise elution method that changes the concentration of the sodium phosphate buffer in the order of 100 mM, 150 mM, 200 mM, 300 mM and 500 mM. This chromatography was performed at room temperature. As shown in FIG. 1, the enzyme showing a β-galactosidase (ONPG) activity was eluted with sodium phosphate buffer solution at a concentration of 100 mM, 150 mM, and 300 to 500 mM, and respective fractions were referred to as fraction 1, fraction 2, and fraction 3 in order. The enzyme contained in the fraction 3 was found to be an almost single protein with a molecular weight of 195 kDa as estimated by SDS-polyacrylamide gel electrophoresis and referred to as β-Gal1.

Then, the fraction 1 was separated and purified by an affinity chromatography. At first the fraction 1 was dialyzed against a 50 mM acetate buffer solution (pH 5.8). The dialyzed enzyme solution was charged to an affinity gel column (p-Aminobenzyl-1-thio-β-D-galactopyranoside-agarose, manufactured by Sigma-Aldrich (St. Louis, Mo., USA) 1.6 cm in diameter, 18 cm in length) which had been equilibrated with the same buffer solution, thereby to elute the unadsorbed protein with the same buffer solution. After that, elution was performed by a linear gradient method of changing the pH from 5.8 to 3.5 at 4° C. (50 mM acetate buffer solution (pH 5.8)/50 mM acetate buffer solution (pH 3.5)). As shown in the fraction 1, enzymes showing a β-galactosidase activity were eluted in a washing fraction and at about pH 4.4, respectively. They showed a nearly single band in SDS-polyacrylamide gel electrophoresis and a molecular weight of 135 kDa and 86 kDa, respectively. The former was referred to as β-Gal2, and the latter was referred to as β-Gal3.

Figure 2:
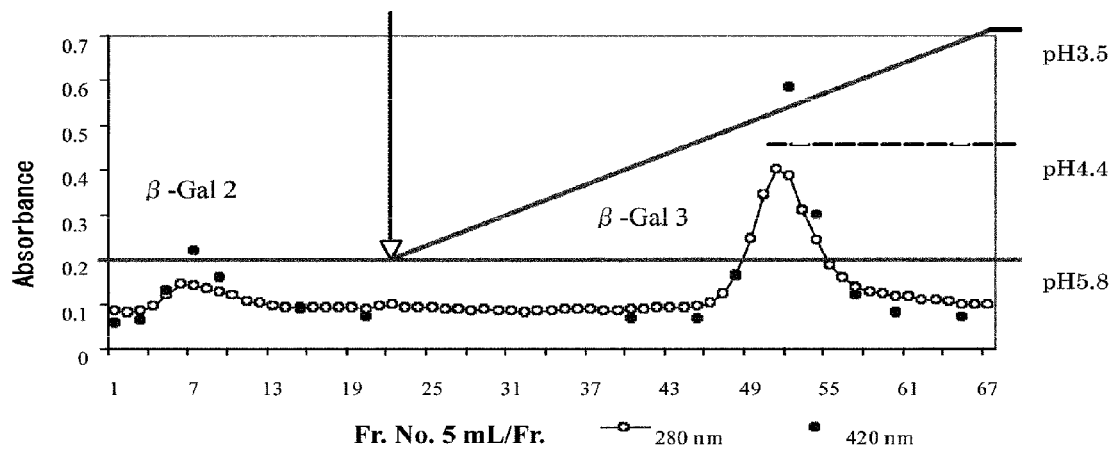
FIG. 2 is an elution pattern of an affinity chromatography of the obtained fraction 1 (see FIG. 1). The absorbance at 280 nm corresponds to the protein concentration and the absorbance at 420 nm measured by the ONPG method corresponds to the β-galactosidase activity.
Figure 3:
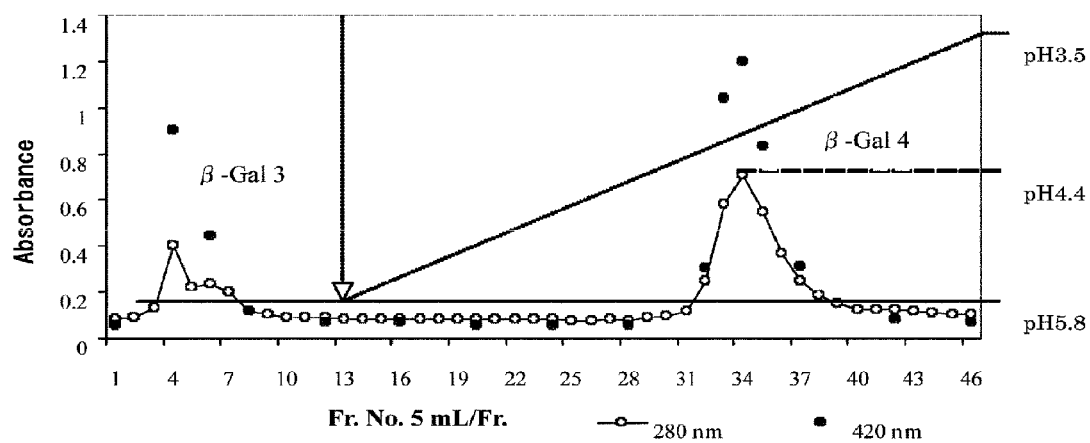
FIG. 3 is an elution pattern of an affinity chromatography of the obtained fraction 2 (see FIG. 1). The absorbance at 280 nm corresponds to the protein concentration and the absorbance at 420 nm measured by the ONPG method corresponds to the β-galactosidase activity.
Figure 4:
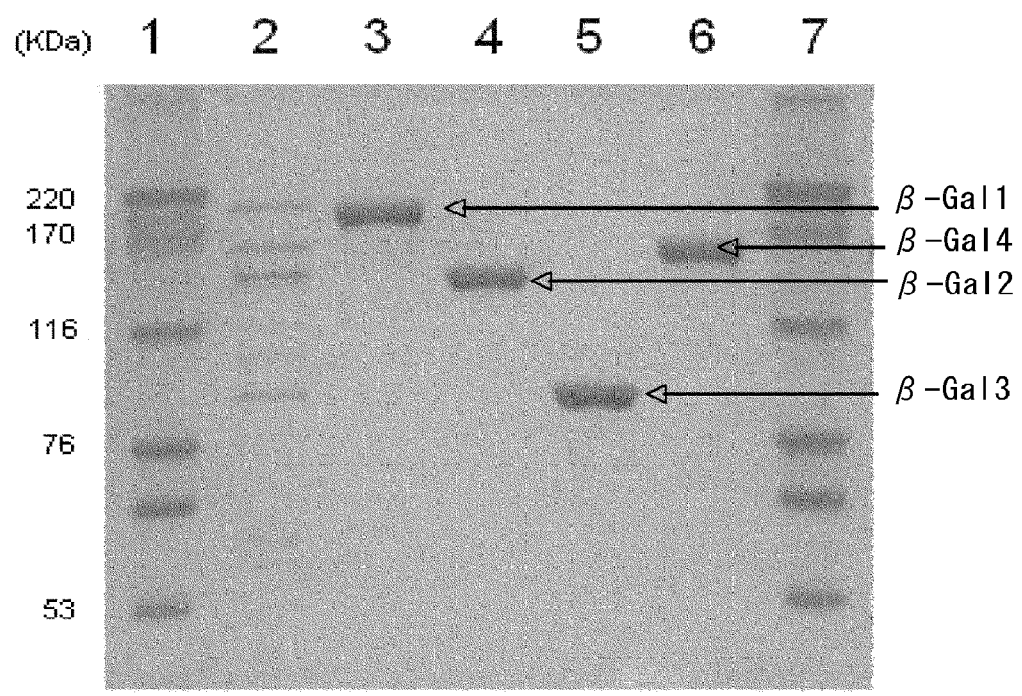
FIG. 4 is the result of an SDS-polyacrylamide gel electrophoresis of four kinds of purified β-galactosidases including β-Gal1 (lane 3), β-Gal2 (lane 4), β-Gal3 (lane 5), and β-Gal4 (lane 6). A crude enzyme powder was provided to the lane 2. The molecular weight of a molecular weight marker (lanes 1 and 7) used is shown in the left end.

On the other hand, fraction 2 was separated and purified by an affinity chromatography in a similar manner to the fraction 1. The fraction 2 was dialyzed against a 50 mM acetate buffer solution (pH 5.8), and charged to the above affinity gel column which had been equilibrated with the same buffer solution. As in FIG. 2, unadsorbed proteins were eluted with the same buffer solution, and then elution was performed by a linear gradient method of changing the pH from 5.8 to 3.5 at 4° C. As shown in FIG. 3, enzymes each showing a β-galactosidase activity were eluted in a washing fraction and at about pH 4.4, respectively. They showed a nearly single band in SDS-polyacrylamide gel electrophoresis and a molecular weight of 86 kDa and 160 kDa, respectively. The former was the same as β-Gal3 and the latter was referred to as β-Gal4. FIG. 4 shows the analytical result of 10% SDS-PAGE of crude enzyme sample (lane 2) as well as purified β-Gal1 (lane 3), β-Gal2 (lane 4), β-Gal3 (lane 5), and β-Gal4 (lane 6).

2. Various Properties of Purified β-Galactosidase Derived from *Bacillus circulans*

The main properties of four kinds of purified β-galactosidases were examined.

(a) Measurement of Specific Activity

An activity when ONPG (final concentration of 0.24%) and lactose (final concentration of 4.88%) were used as a substrate was measured in a 100 mM phosphate buffer solution (pH 6) at 40° C. The results are shown in Table 1. In addition, when ONPG was used as a substrate, an enzyme amount to produce a product, nitrophenol, 1 μmol in one minute under the conditions of 40° C. and pH 6 was defined as 1 U, and when lactose was used as a substrate, an enzyme amount to produce a product, glucose, 1 μmol in one minute under the conditions of 40° C. and pH 6 was defined as 1 U. As shown in Table 1, it is understood that β-Gal1 has a higher hydrolyzing activity against ONPG than lactose, while β-Gal2, 3-Gal3 and β-Gal4 each shows a lower hydrolyzing activity against ONPG than lactose. "GNSVSY-DGERRVNFNEN" recited in Table 1 corresponds to SEQ ID NO: 1 and "SVSYDGERRVNFNEN" recited in Table 1 corresponds SEQ ID NO: 17.

TABLE 1

| Enzyme | Crude enzyme (U/mg) | β-Gal1 (U/mg) | β-Gal2 (U/mg) | β-Gal3 (U/mg) | β-Gal4 (U/mg) |
|---|---|---|---|---|---|
| Specific activity (Substrate; ONPG) | 16.0 | 50.0 | 13.4 | 17.6 | 10.9 |
| Specific activity (Substrate; lactose) | 35.4 | 46.5 | 62.0 | 72.6 | 45.0 |
| Molecular weight (SDS-PAGE) | — | 189.283 kDa (195 kDa) | 134.788 kDa (135 kDa) | 91.027 kDa (86 kDa) | 153.932 kDa (160 kDa) |
| N-Terminal amino acid sequence | — | GNSVSYDGERRVNFNEN (SVSYDGERRVNFNEN) | Same as the left | Same as the left | Same as the left |

(b) Determination of Molecular Weight

The molecular weights of four kinds of β-galactosidases were determined using a MALDI (Matrix Assisted Laser Desorption/Ionization) analyzer. As a sample, a mixed solution of 0.1 μl of 10 mg/ml Sinapinic acid/0.1 μl of 0.7 to 3 mg/ml enzyme solution was used. As a result, β-Gal1 was found to be 189.283 kDa, β-Gal2 was found to be 134.788 kDa, β-Gal3 was found to be 91.027 kDa, and β-Gal4 was found to be 153.932 kDa (see Table 1). In addition, the molecular weights determined by SDS-polyacrylamide gel electrophoresis (FIG. 4) were shown in parentheses in Table 1. The molecular weights that were determined with a mass spectrometer for any enzymes showed a similar result to the molecular weights that were determined from SDS-polyacrylamide gel electrophoresis.

(c) Determination of N-Terminal Amino Acid Sequence

Analysis of the N-terminal amino acid sequence of each of four kinds of β-galactosidases was performed using a protein sequencer. As a result, it was revealed that two kinds of sequences, i.e. GNSVSYDGERRVNFNEN (SEQ ID NO: 1) and SVSYDGERRVNFNEN (SEQ ID NO: 17) were included in β-Gal1. However, the difference between these two amino acid sequences resides in the presence or absence of GN in the N-terminal, and their amino acid sequences were found to be basically the same from each other. Moreover, the N-terminal amino acid sequence of each of β-Gal2, 3-Gal3, and β-Gal4 was similar to that of β-Gal1.

(d) Determination of Internal Amino Acid Sequence

Then, each purified enzyme of β-Gal1, β-Gal2, and β-Gal3 was prepared to 1 to 2 mg/mL, and trypsin (0.5 mg/mL) was added to this, followed by incubation at 37° C. After 48 hours, these enzymes were subjected to a 8% SDS-polyacrylamide gel electrophoresis. A band of 70 kDa was detected from all of such enzymes. The gel after the electrophoresis was transferred to a nitrocellulose membrane for staining with Coomassie Brilliant Blue. A band of 70 kDa derived from each enzyme was cut out from the stained bands, and the amino acid sequence was analyzed by a protein sequencer. As a result, the amino acid sequences of the N-terminal 5 residues of the 70 kDa proteins derived from each enzyme were matched each other. In addition, the amino acid sequence of the N-terminal 15 residues of the 70 kDa protein derived from β-Gal3 was found to be EDRAD-VNIKTKISND (SEQ ID NO: 2).

3. Acquisition of Gene Fragment Encoding β-Galactosidase Derived from *Bacillus circulans*

(a) Isolation of Chromosomal DNA

A chromosomal DNA was prepared from the cell bodies of *Bacillus circulans* ATCC 31382 by the Saito/Miura method (non-patent document 5).

(b) Production of DNA Probe by PCR

Based on the N-terminal amino acid sequence and the internal amino acid sequence, which were determined in the above 2., two kinds of oligonucleotides (SEQ ID NO: 3 and SEQ ID NO: 4) were synthesized and served as a PCR primer. Using these primers, a PCR reaction was performed with a chromosomal DNA of *Bacillus circulans* as a template under the following conditions.

<PCR Reaction Solution>
10×PCR reaction buffer solution (Takara Bio Inc., Shiga, JAPAN) 5.0 μl
dNTP mixture (2.5 mM each, Takara Bio Inc., Shiga, JAPAN) 8.0 μl
25 mM MgCl$_2$ 5.0 μl
50 μM sense primer 0.5 μl
50 μM antisense primer 0.5 μl
Distilled water 29.5 μl
Chromosomal DNA solution (100 μg/mL) 1.0 μl
LA Taq DNA polymerase (Takara Bio Inc., Shiga, JAPAN) 0.5 μl <PCR Reaction Conditions>
Stage 1: Denaturation (95° C., 5 minutes) 1 cycle
Stage 2: Denaturation (95° C., 1 minute) 30 cycles
Annealing (52° C., 1 minute)
Extension (72° C., 1 minute)
Stage 3: Extension (72° C., 10 minutes) 1 cycle After cloning of the obtained DNA fragment of about 0.6 kb into pGEM®-Teasy (Promega, Madison, Wis., USA), identification of the base sequence revealed that a base sequence to encode the partial amino acid sequence mentioned above was found just after a sense primer and just before an antisense primer. This DNA fragment was served as a DNA probe for full length gene cloning.

(c) Construction of Gene Library

As a result of Southern hybridization analysis of the chromosomal DNA derived from *Bacillus circulans*, a single band of about 8.2 kb that hybridizes to a probe DNA was found in the hydrolysate by SpeI. For cloning of this SpeI DNA fragment of about 8.2 kb, a gene library was constructed as follows. The chromosomal DNA prepared in (a) mentioned above was treated with SpeI. The chromosomal DNA 50 vg, 10×M buffer solution 40 μl, distilled water 342.0 μl and SpeI 8.0 μl were mixed together, and treated at 37° C. for 15 hours. The resulting hydrolysate was ligated to SpeI-digested pBluescript II KS+vector (Stratagene, La Jolla, Calif., USA) to obtain a gene library.

(d) Screening of Gene Library

The 0.6 kb DNA fragment obtained in the above (b) was labeled with DIG-High Prime (Roche, Basel, SWITZERLAND). Using this labeled product as a DNA probe, the gene library obtained in the above (c) was screened by a colony hybridization method. A plasmid pBlue-Gal1 was obtained from the resulting positive colony.

(e) Determination of Base Sequence

The base sequence of the plasmid pBlue-Gal1 was determined according to the usual method. The base sequence (5214 bp) that encodes a β-galactosidase derived from Bacillus circulans is shown in SEQ ID NO: 5. In addition, the amino acid sequence (1738 amino acids) that is encoded by SEQ ID NO: 5 is shown in SEQ ID NO: 6. In this amino acid sequence, the N-terminal region amino acid sequence (SEQ ID NO: 1) and the internal amino acid sequence (SEQ ID NO: 2) which were determined in the above 2, were found. Interestingly, the initiation codon in the present gene was thought to be GTG. Moreover, an amino acid sequence that excludes the signal peptide from the amino acid sequence of SEQ ID NO: 6 is shown in SEQ ID NO: 7.

4. Expression of β-Galactosidases β-Gal1, β-Gal2, and β-Gal4 Derived from Bacillus circulans in Escherichia coli (a) Construction of Expression Plasmid in Escherichia coli for β-Galactosidase Since the N-terminal region amino acid sequences of the proteins corresponding to β-Gal1, β-Gal2, and β-Gal4 each having a molecular weight of 189.3 kDa, 134.8 kDa, and 153.9 kDa respectively (values by mass spectrometry) are common among them, a certain oligonucleotide F-Gal (SEQ ID NO: 11) was synthesized based on the DNA sequence to encode such an amino acid sequence. In addition, based on the DNA sequence to encode an each deduced C-terminal region amino acid sequence, three kinds of oligonucleotides R-Gal1, R-Gal2, and R-Gal4 (SEQ ID NO: 12 to SEQ ID NO: 14, respectively) were synthesized and they were served as a PCR primer. A SalI restriction enzyme recognition site was added to the sense primer F-Gal, and a SalI restriction enzyme recognition site was added to the antisense primers R-Gal1, R-Gal2, and R-Gal4. Using these primers and a chromosomal DNA having a β-galactosidase gene as a template, a PCR reaction was performed under the following conditions.

<PCR Reaction Solution>
10×PCR reaction buffer solution (TOYOBO Co., Ltd., Osaka, JAPAN) 5.0 µl
dNTP mixture (2.5 mM each, TOYOBO Co., Ltd., Osaka, JAPAN) 5.0 µl
10 µM sense primer 1.5 µl
10 µM antisense primer 1.5 µl
25 mM MgSO$_4$ 2.0 µl
Distilled water 33.0 µl
Chromosomal DNA solution (200 µg/ml) 1.0 µl
KOD-Plus-DNA polymerase (TOYOBO Co., Ltd., Osaka, JAPAN) 1.0 µl
<PCR Reaction Conditions>
Stage 1: Denaturation (94° C., 2 minutes) 1 cycle
Stage 2: Denaturation (94° C., 15 seconds) 30 cycles
Annealing (57° C., 30 seconds)
Extension (68° C., 5 minutes)

The obtained PCR products were confirmed by the electrophoresis, and desalinated (69 µl) by the ethanol precipitation method. Subsequently, 10×T buffer solution of 15 µl, 0.1% BSA solution of 10 µl, SalI 3 µl, and SalI 3 µl were added to the PCR products, followed by enzymatic treatment at 37° C. for 15 hours. The solution digested with the restriction enzymes was confirmed by the electrophoresis, purified with NucleoSpin® Extract II (NIPPON Genetics Co., Ltd., Tokyo, JAPAN), and β-Gal1, β-Gal2, and β-Gal4 fragments were ligated to a vector pCold II DNA (Takara Bio Inc., Shiga, JAPAN) which had been treated beforehand with SadI and SalI, thereby to obtain expression plasmids pCold-Gal1, pCold-Gal2, and pCold-Gal4.

(b) Expression of β-Galactosidase in Escherichia coli

The expression plasmids pCold-Gal1, pCold-Gal2, and pCold-Gal4 were each introduced into Escherichia coli BL21 Competent Cells (Takara Bio Inc., Shiga, JAPAN). The strains bearing respectively the pCold-Gal1, pCold-Gal2, and pCold-Gal4 into which a target β-galactosidase gene was inserted were selected by colony PCR from the transformants obtained as ampicillin-resistant strains. In addition, a transformant of Escherichia coli BL21 having an expression vector pCold II DNA as a control was also obtained. These transformants were inoculated to an LB medium 1 ml containing ampicillin of 100 µg/mL and cultured until reaching O.D600=0.4 to 1.0 at 37° C. and 170 rpm (previous culture). Subsequently, the preculture solution 300 µl was inoculated to an LB medium 9 ml containing ampicillin of 100 µg/mL and cultured until reaching O.D600=0.4 to 1.0 at 37° C. and 170 rpm. After allowing the culture solution to stand at 15° C. for 30 minutes, 0.1M IPTG 9 µl was added thereto, and culturing (mainculture) was performed at 15° C. and 160 rpm for 24 hours, after which time the cell bodies were collected. The cell bodies were suspended in 100 mM phosphate buffer solution (pH 6.0) 1.0 ml, 0.1 mm glass beads 0.50 g were added, and the cell bodies were disrupted with a multi-beads shocker (Yasui Kikai Corporation, Osaka, JAPAN). The disruption condition was as follows: 3.75 cycles of ON 120 seconds and OFF 60 seconds were repeated. The resulting cell-free extract was centrifuged to obtain a soluble component.

(c) Confirmation of β-Galactosidase Expression

Figure 5:
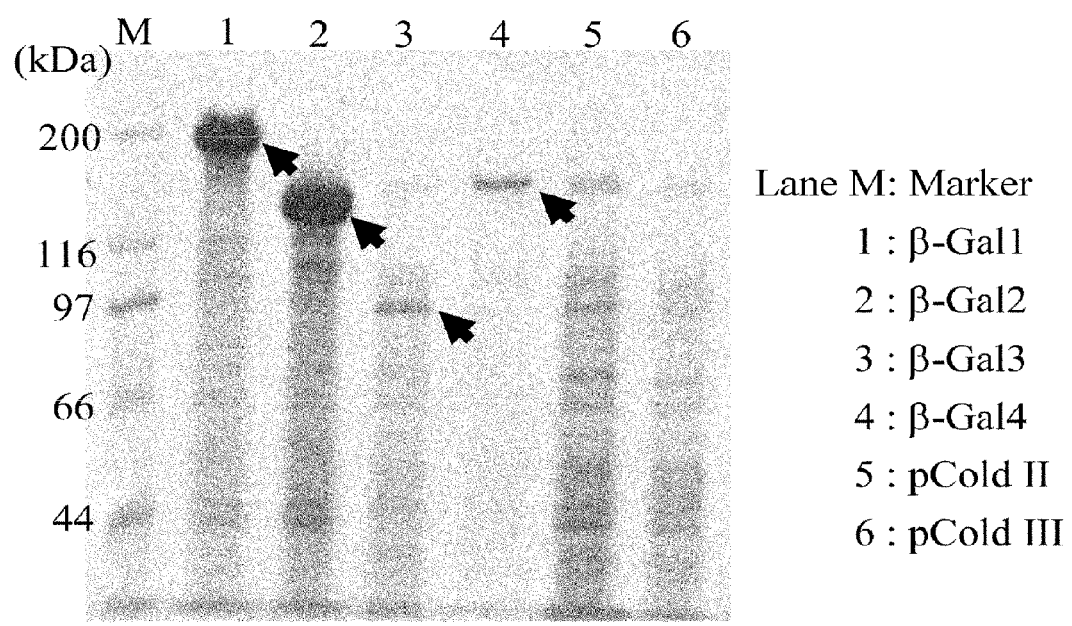
FIG. 5 is the result of an SDS-polyacrylamide gel electrophoresis of a centrifugal supernatant from the cell lysates of an *Escherichia coli* transformant. Lane 1 is β-Gal1, lane 2 is β-Gal2, lane 3 is β-Gal3, and lane 4 is β-Gal4. The lanes 5 and 6 are each a centrifugal supernatant from the cell lysates of a transformant transformed with an *Escherichia coli* vector. The arrow shows an expressed β-galactosidase protein. In the left end, the molecular weight of a molecular weight marker (lane M) used is shown.

The obtained soluble component was subjected to SDS-PAGE. PhastSystem™ (GE Healthcare, Little Chalfont, UK) was used as an electrophoresis device and PhastGel™ Homogeneous 7.5 (GE Healthcare, Little Chalfont, UK) was used as a separation gel. As a result, it was confirmed as shown in FIG. 5 that significant proteins which were considered to be β-Gal1, 3-Gal2, and β-Gal4 respectively were produced in the vicinity of 189 kDa for pCold-Gal1, in the vicinity of 135 kDa for pCold-Gal2, and in the vicinity of 154 kDa for pCold-Gal4. In the case of pCold II DNA as a control, a similar protein production was not confirmed and it was thought that these proteins depended on respective introduction of β-galactosidase genes such as β-Gal1, β-Gal2, and β-Gal4.

In addition, a β-galactosidase activity was measured on the same sample using each of ONPG and lactose as a substrate. The results of the activity measurement are shown in Table 2.

TABLE 2

|  | ONPG-hydrolyzing activity (U/mg) | Lactose-hydrolyzing activity (U/mg) |
| --- | --- | --- |
| pColdII-Gal1 | 31.99 | 34.19 |
| pColdII-Gal2 | 6.40 | 26.43 |
| pColdII-Gal4 | 2.13 | 8.74 |
| pColdII | 0.48 | 0.00 |

In any case, if ONPG was used as a substrate, a β-galactosidase activity that was four or more times greater than the activity of the control was detected, and if lactose was used as a substrate, the apparent β-galactosidase activity was detected in comparison with the control. An expression of the target β-galactosidases β-Gal1, β-Gal2, and β-Gal4 were confirmed.

5. Expression of β-Galactosidase β-Gal3 Derived from *Bacillus circulans* in *Escherichia coli*

(a) Construction of Expression Plasmid for β-Galactosidase in *Escherichia coli*

In the same manner as above, an expression plasmid for β-Gal3 was constructed. Based on the DNA sequence to encode an N-terminal region amino acid sequence and a deduced C-terminal region amino acid sequence of the protein corresponding to β-Gal3 with a molecular weight of 91.0 kDa (the value as estimated by mass spectrometry), two kinds of oligonucleotides (SEQ ID NO: 15 and SEQ ID NO: 16) were synthesized and they were served as a PCR primer. An NdeI restriction enzyme recognition site was added to the sense primer F-Gal3, and an XbaI restriction enzyme recognition site was added to the antisense primer R-Gal3. Using these primers and a chromosomal DNA having a β-galactosidase gene as a template, a PCR reaction was performed under the following conditions.

<PCR Reaction Solution>
10×PCR reaction buffer solution (TOYOBO Co., Ltd., Osaka, JAPAN) 5.0 µl
dNTP mixture (2.5 mM each, TOYOBO Co., Ltd., Osaka, JAPAN) 5.0 µl
10 µM sense primer 1.5 µl
10 µM antisense primer 1.5 µl
25 mM MgSO$_4$ 2.0 µl
Distilled water 33.0 µl
Chromosomal DNA solution (200 µg/ml) 1.0 µL
KOD-Plus-DNA polymerase (TOYOBO Co., Ltd., Osaka, JAPAN) 1.0 µL <PCR Reaction Conditions>
Stage 1: Denaturation (94° C., 2 minutes) 1 cycle
Stage 2: Denaturation (94° C., 15 seconds) 30 cycles
Annealing (57° C., 30 seconds)
Extension (68° C., 3 minutes)

The obtained PCR products were confirmed by the electrophoresis, then and desalinated (84 µl) by the ethanol precipitation method. Subsequently, a suitable buffer solution of 10 µl as well as NdeI 3 µl and XbaI 3 µl were added to the PCR products, followed by enzymatic treatment at 37° C. for 15 hours. The solution digested with the restriction enzymes was confirmed by the electrophoresis, purified with NucleoSpin® Extract II (NIPPON Genetics Co., Ltd., Tokyo, JAPAN), and then ligated to a vector pCold III DNA which had been treated beforehand with NdeI and XbaI, thereby to obtain an expression plasmid pCold-Gal3.

(b) Expression of β-Galactosidase in *Escherichia coli*

The expression plasmid pCold-Gal3 was introduced into *Escherichia coli* BL21 Competent Cells. A strain bearing pCold-Gal3 into which a target β-galactosidase gene was inserted was selected by colony PCR from the transformants obtained as ampicillin-resistant strains. In addition, a transformant of *Escherichia coli* BL21 having an expression vector pCold III DNA as a control was also obtained. These transformants were inoculated to an LB medium 1 ml containing ampicillin of 100 µg/mL and cultured until reaching O.D600=0.4 to 1.0 at 37° C. and 170 rpm (previous culture). Subsequently, the preculture solution 300 µl was inoculated to an LB medium 9 ml containing ampicillin of 100 µg/mL and cultured until reaching O.D600=0.4 to 1.0 at 37° C. and 170 rpm. After treatment of the culture solution at 15° C. for 30 minutes, 0.1M IPTG 9 µl was added thereto, and culturing (mainculture) was performed at 15° C. and 160 rpm for 24 hours, after which time the cell bodies were collected. The cell bodies were suspended in 100 mM phosphate buffer solution (pH 6.0) 1.0 ml, φ0.1 mm glass beads 0.50 g were added, and the cell bodies were disrupted with a multi-beads shocker. The disruption condition was as follows: 3.75 cycles of ON 120 seconds and OFF 60 seconds were repeated. The resulting cell-free extract was centrifuged to obtain a soluble component.

(c) Confirmation of β-Galactosidase Expression

The soluble component obtained in the same manner as in 4, was subjected to SDS-PAGE. PhastSystem™ (GE Healthcare, Little Chalfont, UK) was used as an electrophoresis device and PhastGel™ Homogeneous 7.5 (GE Healthcare, Little Chalfont, UK) was used as a separation gel. As a result, as shown in FIG. 5, a significant production of a protein that was considered to be β-Gal3 was confirmed in the vicinity of 91 kDa for pCold-Gal3. In the case of pCold III DNA as a control, a similar protein production was not confirmed and thus it was thought that the protein depended on the introduction of β-galactosidase gene β-Gal3.

In addition, a β-galactosidase activity was measured on the same sample using each of ONPG and lactose as a substrate. The measurement results of the activity are shown in Table 3. A β-galactosidase activity that was five or more times greater than the activity of the control was detected when ONPG was used as a substrate, and a β-galactosidase activity that was 200 or more times greater than the activity of the control was detected when lactose was used as a substrate. An expression of the target β-galactosidase β-Gal3 was confirmed.

TABLE 3

| | ONPG-hydrolyzing activity (U/mg) | Lactose-hydrolyzing activity (U/mg) |
|---|---|---|
| pColdIII-Gal3 | 1.79 | 6.01 |
| pColdIII | 0.34 | 0.03 |

INDUSTRIAL APPLICABILITY

The present invention provides a novel β-galactosidase derived from *Bacillus circulans*. The β-galactosidase of the invention is industrially useful and can be used, for example, in the production of milk, dairy products, fermented dairy products, galacto-oligosaccharides or supplements for foods.

The present invention is not limited at all to the description of the above embodiments and Examples. A variety of modifications, which should not depart from the scope of the claims and which can be easily conceived by a person skilled in the art, are included in the invention.

Contents of the theses, unexamined patent publications, examined patent publications, and other published documents referred to in this specification are herein incorporated by reference in their entirety.

[Sequence List Free Text]

SEQ ID NO: 3, SEQ ID NO: 4, and SEQ ID NO: 11 to SEQ ID NO: 16: Description of Artificial Sequence: Primer

The invention claimed is:

1. A method for producing a low-lactose milk, a galacto-oligosaccharide that is an intestinal *bifidobacterium* growth factor, or a low lactose dairy product, the method comprising:

treating lactose or a galacto-oligosaccharide with a β-galactosidase enzyme, wherein the β-galactosidase enzyme comprises a polypeptide selected from the group consisting of SEQ ID NO: 7, SEQ ID NO: 8, SEQ ID NO: 9, SEQ ID NO: 10, a polypeptide having at least 90% identity to SEQ ID NO: 7, a polypeptide having at least 90% identity to SEQ ID NO: 8, a polypeptide having at least 90% identity to SEQ ID NO: 9, and a polypeptide having at least 90% identity to SEQ ID NO: 10, thereby producing a low-lactose milk, a galacto-oligosaccharide that is an intestinal *bifidobacterium* growth factor, or a low lactose dairy product.

2. The method of claim 1, wherein the polypeptide has at least 95% sequence identity to SEQ ID NOs: 7, 8, 9, or 10.

3. The method of claim 1, wherein the polypeptide has at least 98% sequence identity to SEQ ID NOs: 7, 8, 9, or 10.

4. The method of claim 1, wherein the polypeptide has at least 99% sequence identity to SEQ ID NOs: 7, 8, 9, or 10.

5. A method for producing a product selected from the group consisting of a low-lactose milk, a galacto-oligosaccharide that is an intestinal *bifidobacterium* growth factor, and a medicine or supplement for patients with lactose intolerance, comprising:

treating lactose containing material or a galacto-oligosaccharide with an enzyme preparation comprising a mixture of isolated β-galactosidase enzymes obtained from *Bacillus circulans*, wherein the mixture of enzymes comprises enzymes selected from the group consisting of SEQ ID NO: 8, SEQ ID NO: 9, SEQ ID NO: 10, a polypeptide having at least 90% identity to SEQ ID NO: 8, a polypeptide having at least 90% identity to SEQ ID NO: 9, and a polypeptide having at least 90% identity to SEQ ID NO: 10, wherein SEQ ID NO: 8, SEQ ID NO: 9, and SEQ ID NO: 10 are c-terminus truncations of native β-galactosidase, and wherein the enzymes have decreased p-nitrophenyl-β-D-galactopyranoside (ONPG) hydrolyzing activity relative to the native β-galactosidase and/or increased lactose hydrolyzing activity relative to native β-galactosidase.

6. The method of claim 5, wherein the polypeptide has at least 95% sequence identity to SEQ ID NOs: 8, 9, or 10.

7. The method of claim 5, wherein the polypeptide has at least 98% sequence identity to SEQ ID NOs: 8, 9, or 10.

8. The method of claim 5, wherein the polypeptide has at least 99% sequence identity to SEQ ID NOs: 8, 9, or 10.

9. The method of claim 5, wherein each of the enzyme has an increased lactose hydrolyzing activity relative to the native β-galactosidase.

10. The method of claim 1, wherein the lactose containing material is milk.

11. The method of claim 1, wherein:
the galacto-oligosaccharide is Gal-(Gal)-Glc;
n is 0 to 3;
the Gal is a galactose residue;
the Glc is a glucose residue; and
the bond mode is α1-3, α1-6, β1-6, β1-3, β1-4, or β1-2.

12. The method of claim 5, wherein the lactose containing material is milk.

13. The method of claim 5, wherein:
the galacto-oligosaccharide is Gal-(Gal)-Glc;
n is 0 to 3;
the Gal is a galactose residue;
the Glc is a glucose residue; and
the bond mode is α1-3, α1-6, β1-6, β1-3, β1-4, or β1-2.

* * * * *

SEQUENCE LISTING

<160> NUMBER OF SEQ ID NOS: 18

<210> SEQ ID NO 1
<211> LENGTH: 17
<212> TYPE: PRT
<213> ORGANISM: Bacillus circulans

<400> SEQUENCE: 1

Gly Asn Ser Val Ser Tyr Asp Gly Glu Arg Arg Val Asn Phe Asn Glu
1               5                   10                  15

Asn

<210> SEQ ID NO 2
<211> LENGTH: 15
<212> TYPE: PRT
<213> ORGANISM: Bacillus circulans

<400> SEQUENCE: 2

Glu Asp Arg Ala Asp Val Asn Ile Lys Thr Lys Ile Ser Asn Asp
1               5                   10                  15

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ggcaatagcg tgagctatga tgg                                          23

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gattttcgtt ttgatattca catcggc                                      27

<210> SEQ ID NO 5
<211> LENGTH: 5214
<212> TYPE: DNA
<213> ORGANISM: Bacillus circulans

<400> SEQUENCE: 5
gtgaaaaaag cgattagctg cgttttttta atttcagcac tgattctatc aagctttcaa    60
gtccctgtac agggacaagc catgtcaaaa acgacatcgg cagcaggaaa cagtgtgagc   120
tatgatggag agagacgagt gaattttaac gagaattggc gatttcaacg agaaaccaat   180
ggaagtattg ccggagcaca gaatcctggc tttgacgatt cctcctggcg gaaattaaat   240
ctgccgcatg actggagtat tgaattagat tttaataaaa attctcttgc cacacatgaa   300
ggcggttatt tggacggcgg aatcggctgg taccgaaaaa cctttacaat cccggaatcg   360
atgaagggaa aacgaatttc gcttgatttt gatggcgttt acatgaacag caccacctat   420
ctaaacgggg aagtgctcgg gacctatccg tttggttata tgcctttttc ctatgatatt   480
tccgacaaac tttataaaga tggcagggcg aatgtccttg ttgtcaaagt caataacacc   540
cagccgagca gccgctggta ttcggggagc gggatctacc ggaatgtcta tctcactgtg   600
accgatccca tccatgtggc tcgctacgga acatttgtga caacacccaa tttagagaaa   660

```
tcgataaaag aagacagggc tgatgtgaac atcaagacga aaatcagtaa cgatgctgct    720
gaggcgaaac aggtaaagat taaatcaacc atctacgatg gggctgggaa caccgtacag    780
acagtggaaa cggaggaaaa aacagctgcc gccggcacgg tgactccgtt cgaacaaaac    840
acagtcatca agcagccgaa gctttggagc attgacaagc cttatcgata taaccttgtt    900
acagaagtca tcgttggcgg gcaaacggtg gatacgtatg aaacaaaatt tggtgtcagg    960
tatttcaaat ttgatgaaaa cgaaggcttt tccttaaatg gagagtatat gaagctgcac   1020
ggcgtttcga tgcaccatga tttaggggcg cttggggcgg caacgaatgc acgcggcgtg   1080
gaaagacaaa tgcagattat gaaggatatg ggggtcaatg ccatcagggt tacccacaac   1140
ccggcatcac cggaactgct ggaggcagct aataaattag gctattcat catcgaggag    1200 gcatttgaca gctgggccca gtcaaagaaa ccctatgact atggccgttt tttcaatgca   1260
tgggctgagc acgacattaa ggaaatggtc gatcggggca aaaacgaacc agctattatc   1320
atgtggtcga tcggaaatga aatatatgat acgaccaatg ccgctggtgt ggaaacagca   1380
cgaaatttag tgggttgggt aaaagaaatt gacaccacaa ggccgacaac gatcggcgag   1440
gataaaaccc gcggagacaa agtaaatgtt acacctatca acagctacat caaggagatt   1500
tttaatattg tcgatgtggt cggactgaac tacagcgaga caactatga tggctaccac    1560 aagcagaatc cgtcatggaa gctgtacggc tcggagacgt cctcggcaac ccgttcgcgt   1620
ggtgtctaca cgcatccgta ccagtataac caaagcacaa agtatgctga tttacagcaa   1680
tcctcttatg acaatgacta tgtcggctgg ggacgaactg cagaagatgc atggaaatat   1740
gaccgcgacc tgaagcatat tgcagggcaa tttatctgga ccggctttga ttatattggc   1800
gagccgacgc catattataa ttcctatcct gcaaaaagct cctatttggg tgctgtggat   1860
acggctggtt ttccaaagga tattttctac tattaccaaa gccaatggaa aaaggagcct   1920
atggtccacc tgctgccgca ttggaactgg aaggaagggg aaaaggtccg cgtcttagct   1980
tataccaatg caagtaaggt tgaacttgtt ctaaatggtg aatcgttagg ggagaagaac   2040
tatgacaaca aacaaacctc ctggggagca ccatacaaag aaacaaagga tggaaaaacc   2100
tatttggagt gggccgtacc atttaaaccg ggcaaattag aagccgtcgc caaggatgaa   2160
aacggcaaag tgatcgcccg cgatcaggta gtgaccgctg gtgagccagc ctctgtcaga   2220
ttaacggctg atcgtaaggt ggtcaaggcg gacggtacgg atctgtcgtt tattacagca   2280
gacattgttg atagtaaagg gattgttgtc ccggatgccg atcatctgat tacatttaac   2340
gtaacgggcc aaggggaatt ggccggggtt gataacggaa acgcgtccag tgtggagcgt   2400
tacaaggaca acaagcgcaa ggctttcagc gggaaagcat tggcgattgt tcaatcaagt   2460
aagctttctg gaaaaattac ggtccatgcg tcagtggcag ggctttcgag cgattccacg   2520 agcgtatttta cggtaacgcc agctgaccat gacaaaaaga ttgtagctgg gattgatgat   2580
gttaacctta ctgtcgatgt caatgaagca ccaaagcttc cttcagaaat caaggtttat   2640
tacagtgatg agagtgcagc tgcgaagaat gtgacttggg atgaggtgga tccaaagcag   2700
tacagcactg ttggtgaatt cacagtggaa ggcagtgtcg agggaacttc gctgaaggca   2760
aaggcatttg ttattgtcaa aggaattgtc gccgtcaagc cttattcaac ggcaacaaag   2820
gttggtgtac agccggtgct gcctgaaaaa gcaacccttc tttacagtga tggaacaacc   2880
aagggagcaa ctgtcacgtg ggatgagatc cctgaggaca agctggcaaa agagggccgg   2940
tttaccgtcg agggcagtgt ggagggaaca gacctcaagg ctaatgtcta tgtcagggtg   3000
```

-continued

| | |
|---|---|
| acaaatgaag taaaatcagt gaatattatg cttcaggagc agggttcagc ttatccaaag | 3060 |
| ctcgaagcta cttttaccaa tccagctgac aatcttcagc atttgaacga tggcatcaag | 3120 |
| agctatacca ataacccggt caaccgctgg acgaactgga caagaacacc gcgtgatgct | 3180 |
| ggtgactcga ttacagttaa ttttggcaag aagcatgtga ttaataatct agatttattt | 3240 |
| gttttaccg acagcggcac ggtggttcca gaaaaggcag aggtccaata ttgggatgga | 3300 |
| acggcgtgga aggatgtcga aaatctaaca cagccatcgc catatgtggt agagaaaaat | 3360 |
| gaacttacat ttgatgcggt cgcgacagaa aagctgaaat tccatttgac accatctgtg | 3420 |
| aaagggaaat tcctagctct aacggaagca gaggtgtacg ccgatcagat tgtgatgggt | 3480 |
| gaaacagcaa aacttcaaag tattacggtg aatgggaaag cattagaagg ctttgatcac | 3540 |
| gctaaaaaga attatgaact tgtacttcca tatggaagcg agcttcctaa gattgaggcg | 3600 |
| gctgctgccg acaatgcaac tgtcaccatt ttaccggcat tctcctatcc gggaacagca | 3660 |
| aaactatttg tcacttcaga ggatgggaag gtaactactg agtacagtat tggtgtttct | 3720 |
| acagaagagc caaagctcgt ctccgcagag ttatccgcgg acaagacgaa tgtcatggag | 3780 |
| gacgatatca tcgatctgaa ggtaattggt ctcttcgaaa gcaaggaaaa gattgatgtg | 3840 |
| accgacagcc agccgacata tgaatttgac cagcagatta ttaaaattga aggcaataag | 3900 |
| ctgtatgcgc tggaaacagg aaatgtcaag gtgaaagtga cggtgacata taagggtgtg | 3960 |
| agtgtcacaa cacctgcgct tgagtttacg atcgcgaaaa ccctgctcc aaaatacatt | 4020 |
| acgagcttag agcctgtcac ggttgttgtt aaaaaaggag aagcgccgga gcttccagca | 4080 |
| acggttgtgg cccattataa ccgaggaatc ccgcgggatg ttaaggtgaa gtgggaaaga | 4140 |
| atcaatccgt ctaagtacca gcagctaggc gagtttaccg tatctggcat ggtggaaggg | 4200 |
| accgatataa aagcccaagc aaagtgatt gtaaagggg ctgttgcggt cgaggatatt | 4260 |
| agaatggctg tgctgttaaa gcaaatgcca cagctgccgg gcaaggttac agtctattat | 4320 |
| agtgacggag cggaagaaca aagagcggtc aagtgggagg aaatcccgca ggaggaactc | 4380 |
| gagaatgtcg gtgaatttaa ggttaaaggt gatgttaatg gagtgaagct gaaagcaaca | 4440 |
| gccactattc gagtaaccga tgaagtcggc ggcgagcaga atatcagccg ggctaaaaat | 4500 |
| ggttatgaat acccgaaggc tgaagcttcc tttaccaaca atggccctgg atcaagcgat | 4560 |
| cgaatcgagg ccatcaatga tgacgtgatc tcctacgagg ctaatccgca taatcgctgg | 4620 |
| acgaattggc agccggtacc gcgtgcaggg gactgggttt ctatcaccctt tggagactat | 4680 |
| gagcctacgg aatatgatgt tgatagcatg gagatccact ggttcgcgga tcatgggacc | 4740 |
| tcgtatccag agcgtttcca aatcgaatat aaatccggtg atagctggaa ggaagtcacc | 4800 |
| agcctgaaaa gcgatccagc ctctccggcc ttgggtaagg caaatgtcta tagctttgat | 4860 |
| cgagtaaaaa catcggctat acgagtgaaa atgacagcac aagccggcaa aagcttagcc | 4920 |
| attaccgagc tgaaagtatt ttcaaaatgg ccaaaggcag gtaccgaacc agaggtgacc | 4980 |
| gatattaagg tcggaggaaa atcgattctg gaggactttg aacaaaaagg cgatcactat | 5040 |
| gaagtaacga ttgatgcagg agatgcgaat gtaatgccga aaatcaatgt aaaggctaag | 5100 |
| gaccagacga gtattacgat tgtgccagca gttacctctc catccacggc aaaggtaatt | 5160 |
| gctaaatccg aggatggcaa gaaagtgaag gtctatagca ttcactataa ataa | 5214 |

<210> SEQ ID NO 6
<211> LENGTH: 1737
<212> TYPE: PRT
<213> ORGANISM: Bacillus circulans

<400> SEQUENCE: 6

```
Val Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
            100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
            195                 200                 205

Tyr Gly Thr Phe Val Thr Thr Pro Asn Leu Glu Lys Ser Ile Lys Glu
        210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Gly
            260                 265                 270

Thr Val Thr Pro Phe Glu Gln Asn Thr Val Ile Lys Gln Pro Lys Leu
        275                 280                 285

Trp Ser Ile Asp Lys Pro Tyr Arg Tyr Asn Leu Val Thr Glu Val Ile
290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
        355                 360                 365

Asp Met Gly Val Asn Ala Ile Arg Val Thr His Asn Pro Ala Ser Pro
370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
```

```
            405                 410                 415
Phe Phe Asn Ala Trp Ala Glu His Asp Ile Lys Glu Met Val Asp Arg
            420                 425                 430
Gly Lys Asn Glu Pro Ala Ile Ile Met Trp Ser Ile Gly Asn Glu Ile
            435                 440                 445
Tyr Asp Thr Thr Asn Ala Ala Gly Val Glu Thr Ala Arg Asn Leu Val
            450                 455                 460
Gly Trp Val Lys Glu Ile Asp Thr Thr Arg Pro Thr Thr Ile Gly Glu
465                 470                 475                 480
Asp Lys Thr Arg Gly Asp Lys Val Asn Val Thr Pro Ile Asn Ser Tyr
                485                 490                 495
Ile Lys Glu Ile Phe Asn Ile Val Asp Val Val Gly Leu Asn Tyr Ser
            500                 505                 510
Glu Asn Asn Tyr Asp Gly Tyr His Lys Gln Asn Pro Ser Trp Lys Leu
            515                 520                 525
Tyr Gly Ser Glu Thr Ser Ser Ala Thr Arg Ser Arg Gly Val Tyr Thr
            530                 535                 540
His Pro Tyr Gln Tyr Asn Gln Ser Thr Lys Tyr Ala Asp Leu Gln Gln
545                 550                 555                 560
Ser Ser Tyr Asp Asn Asp Tyr Val Gly Trp Gly Arg Thr Ala Glu Asp
                565                 570                 575
Ala Trp Lys Tyr Asp Arg Asp Leu Lys His Ile Ala Gly Gln Phe Ile
            580                 585                 590
Trp Thr Gly Phe Asp Tyr Ile Gly Glu Pro Thr Pro Tyr Tyr Asn Ser
            595                 600                 605
Tyr Pro Ala Lys Ser Ser Tyr Phe Gly Ala Val Asp Thr Ala Gly Phe
            610                 615                 620
Pro Lys Asp Ile Phe Tyr Tyr Gln Ser Gln Trp Lys Lys Glu Pro
625                 630                 635                 640
Met Val His Leu Leu Pro His Trp Asn Trp Lys Glu Gly Glu Lys Val
                645                 650                 655
Arg Val Leu Ala Tyr Thr Asn Ala Ser Lys Val Glu Leu Val Leu Asn
            660                 665                 670
Gly Glu Ser Leu Gly Glu Lys Asn Tyr Asp Asn Lys Gln Thr Ser Trp
            675                 680                 685
Gly Ala Pro Tyr Lys Glu Thr Lys Asp Gly Lys Thr Tyr Leu Glu Trp
            690                 695                 700
Ala Val Pro Phe Lys Pro Gly Lys Leu Glu Ala Val Ala Lys Asp Glu
705                 710                 715                 720
Asn Gly Lys Val Ile Ala Arg Asp Gln Val Val Thr Ala Gly Glu Pro
                725                 730                 735
Ala Ser Val Arg Leu Thr Ala Asp Arg Lys Val Val Lys Ala Asp Gly
                740                 745                 750
Thr Asp Leu Ser Phe Ile Thr Ala Asp Ile Val Asp Ser Lys Gly Ile
            755                 760                 765
Val Val Pro Asp Ala Asp His Leu Ile Thr Phe Asn Val Thr Gly Gln
            770                 775                 780
Gly Glu Leu Ala Gly Val Asp Asn Gly Asn Ala Ser Ser Val Glu Arg
785                 790                 795                 800
Tyr Lys Asp Asn Lys Arg Lys Ala Phe Ser Gly Lys Ala Leu Ala Ile
                805                 810                 815
Val Gln Ser Ser Lys Leu Ser Gly Lys Ile Thr Val His Ala Ser Val
            820                 825                 830
```

```
Ala Gly Leu Ser Ser Asp Ser Thr Ser Val Phe Thr Val Thr Pro Ala
        835                 840                 845

Asp His Asp Lys Lys Ile Val Ala Gly Ile Asp Asp Val Asn Leu Thr
850                 855                 860

Val Asp Val Asn Glu Ala Pro Lys Leu Pro Ser Glu Ile Lys Val Tyr
865                 870                 875                 880

Tyr Ser Asp Glu Ser Ala Ala Ala Lys Asn Val Thr Trp Asp Glu Val
                885                 890                 895

Asp Pro Lys Gln Tyr Ser Thr Val Gly Glu Phe Thr Val Glu Gly Ser
                900                 905                 910

Val Glu Gly Thr Ser Leu Lys Ala Lys Ala Phe Val Ile Val Lys Gly
            915                 920                 925

Ile Val Ala Val Lys Pro Tyr Ser Thr Ala Thr Lys Val Gly Val Gln
        930                 935                 940

Pro Val Leu Pro Glu Lys Ala Thr Leu Leu Tyr Ser Asp Gly Thr Thr
945                 950                 955                 960

Lys Gly Ala Thr Val Thr Trp Asp Glu Ile Pro Glu Asp Lys Leu Ala
                965                 970                 975

Lys Glu Gly Arg Phe Thr Val Glu Gly Ser Val Glu Gly Thr Asp Leu
            980                 985                 990

Lys Ala Asn Val Tyr Val Arg Val  Thr Asn Glu Val Lys  Ser Val Asn
        995                 1000                1005

Ile Met  Leu Gln Glu Gln Gly  Ser Ala Tyr Pro Lys  Leu Glu Ala
    1010                1015                1020

Thr Phe  Thr Asn Pro Ala Asp  Asn Leu Gln His Leu  Asn Asp Gly
    1025                1030                1035

Ile Lys  Ser Tyr Thr Asn Asn  Pro Val Asn Arg Trp  Thr Asn Trp
    1040                1045                1050

Thr Arg  Thr Pro Arg Asp Ala  Gly Asp Ser Ile Thr  Val Asn Phe
    1055                1060                1065

Gly Lys  Lys His Val Ile Asn  Asn Leu Asp Leu Phe  Val Phe Thr
    1070                1075                1080

Asp Ser  Gly Thr Val Val Pro  Glu Lys Ala Glu Val  Gln Tyr Trp
    1085                1090                1095

Asp Gly  Thr Ala Trp Lys Asp  Val Glu Asn Leu Thr  Gln Pro Ser
    1100                1105                1110

Pro Tyr  Val Val Glu Lys Asn  Glu Leu Thr Phe Asp  Ala Val Ala
    1115                1120                1125

Thr Glu  Lys Leu Lys Phe His  Leu Thr Pro Ser Val  Lys Gly Lys
    1130                1135                1140

Phe Leu  Ala Leu Thr Glu Ala  Glu Val Tyr Ala Asp  Gln Ile Val
    1145                1150                1155

Met Gly  Glu Thr Ala Lys Leu  Gln Ser Ile Thr Val  Asn Gly Lys
    1160                1165                1170

Ala Leu  Glu Gly Phe Asp His  Ala Lys Lys Asn Tyr  Glu Leu Val
    1175                1180                1185

Leu Pro  Tyr Gly Ser Glu Leu  Pro Lys Ile Glu Ala  Ala Ala Ala
    1190                1195                1200

Asp Asn  Ala Thr Val Thr Ile  Leu Pro Ala Phe Ser  Tyr Pro Gly
    1205                1210                1215

Thr Ala  Lys Leu Phe Val Thr  Ser Glu Asp Gly Lys  Val Thr Thr
    1220                1225                1230
```

-continued

Glu Tyr Ser Ile Gly Val Ser Thr Glu Pro Lys Leu Val Ser
    1235                1240                1245

Ala Glu Leu Ser Ala Asp Lys Thr Asn Val Met Glu Asp Asp Ile
    1250                1255                1260

Ile Asp Leu Lys Val Ile Gly Leu Phe Glu Ser Lys Glu Lys Ile
    1265                1270                1275

Asp Val Thr Asp Ser Gln Pro Thr Tyr Glu Phe Asp Gln Gln Ile
    1280                1285                1290

Ile Lys Ile Glu Gly Asn Lys Leu Tyr Ala Leu Glu Thr Gly Asn
    1295                1300                1305

Val Lys Val Lys Val Thr Val Thr Tyr Lys Gly Val Ser Val Thr
    1310                1315                1320

Thr Pro Ala Leu Glu Phe Thr Ile Ala Lys Asn Pro Ala Pro Lys
    1325                1330                1335

Tyr Ile Thr Ser Leu Glu Pro Val Thr Val Val Lys Lys Gly
    1340                1345                1350

Glu Ala Pro Glu Leu Pro Ala Thr Val Val Ala His Tyr Asn Arg
    1355                1360                1365

Gly Ile Pro Arg Asp Val Lys Val Lys Trp Glu Arg Ile Asn Pro
    1370                1375                1380

Ser Lys Tyr Gln Gln Leu Gly Glu Phe Thr Val Ser Gly Met Val
    1385                1390                1395

Glu Gly Thr Asp Ile Lys Ala Gln Ala Lys Val Ile Val Lys Gly
    1400                1405                1410

Ala Val Ala Val Glu Asp Ile Arg Met Ala Val Leu Leu Lys Gln
    1415                1420                1425

Met Pro Gln Leu Pro Gly Lys Val Thr Val Tyr Tyr Ser Asp Gly
    1430                1435                1440

Ala Glu Glu Gln Arg Ala Val Lys Trp Glu Glu Ile Pro Gln Glu
    1445                1450                1455

Glu Leu Glu Asn Val Gly Glu Phe Lys Val Lys Gly Asp Val Asn
    1460                1465                1470

Gly Val Lys Leu Lys Ala Thr Ala Thr Ile Arg Val Thr Asp Glu
    1475                1480                1485

Val Gly Gly Glu Gln Asn Ile Ser Arg Ala Lys Asn Gly Tyr Glu
    1490                1495                1500

Tyr Pro Lys Ala Glu Ala Ser Phe Thr Asn Asn Gly Pro Gly Ser
    1505                1510                1515

Ser Asp Arg Ile Glu Ala Ile Asn Asp Asp Val Ile Ser Tyr Glu
    1520                1525                1530

Ala Asn Pro His Asn Arg Trp Thr Asn Trp Gln Pro Val Pro Arg
    1535                1540                1545

Ala Gly Asp Trp Val Ser Ile Thr Phe Gly Asp Tyr Glu Pro Thr
    1550                1555                1560

Glu Tyr Asp Val Asp Ser Met Glu Ile His Trp Phe Ala Asp His
    1565                1570                1575

Gly Thr Ser Tyr Pro Glu Arg Phe Gln Ile Glu Tyr Lys Ser Gly
    1580                1585                1590

Asp Ser Trp Lys Glu Val Thr Ser Leu Lys Ser Asp Pro Ala Ser
    1595                1600                1605

Pro Ala Leu Gly Lys Ala Asn Val Tyr Ser Phe Asp Arg Val Lys
    1610                1615                1620

Thr Ser Ala Ile Arg Val Lys Met Thr Ala Gln Ala Gly Lys Ser

```
            1625                1630                1635

Leu Ala Ile Thr Glu Leu Lys Val Phe Ser Lys Trp Pro Lys Ala
        1640                1645                1650

Gly Thr Glu Pro Glu Val Thr Asp Ile Lys Val Gly Gly Lys Ser
    1655                1660                1665

Ile Leu Glu Asp Phe Glu Gln Lys Gly Asp His Tyr Glu Val Thr
    1670                1675                1680

Ile Asp Ala Gly Asp Ala Asn Val Met Pro Lys Ile Asn Val Lys
    1685                1690                1695

Ala Lys Asp Gln Thr Ser Ile Thr Ile Val Pro Ala Val Thr Ser
1700                1705                1710

Pro Ser Thr Ala Lys Val Ile Ala Lys Ser Glu Asp Gly Lys Lys
    1715                1720                1725

Val Lys Val Tyr Ser Ile His Tyr Lys
    1730                1735

<210> SEQ ID NO 7
<211> LENGTH: 1702
<212> TYPE: PRT
<213> ORGANISM: Bacillus circulans

<400> SEQUENCE: 7

Gly Asn Ser Val Ser Tyr Asp Gly Glu Arg Arg Val Asn Phe Asn Glu
1               5                   10                  15

Asn Trp Arg Phe Gln Arg Glu Thr Asn Gly Ser Ile Ala Gly Ala Gln
                20                  25                  30

Asn Pro Gly Phe Asp Asp Ser Ser Trp Arg Lys Leu Asn Leu Pro His
            35                  40                  45

Asp Trp Ser Ile Glu Leu Asp Phe Asn Lys Asn Ser Leu Ala Thr His
        50                  55                  60

Glu Gly Gly Tyr Leu Asp Gly Ile Gly Trp Tyr Arg Lys Thr Phe
65                  70                  75                  80

Thr Ile Pro Glu Ser Met Lys Gly Lys Arg Ile Ser Leu Asp Phe Asp
                85                  90                  95

Gly Val Tyr Met Asn Ser Thr Thr Tyr Leu Asn Gly Glu Val Leu Gly
            100                 105                 110

Thr Tyr Pro Phe Gly Tyr Asn Ala Phe Ser Tyr Asp Ile Ser Asp Lys
        115                 120                 125

Leu Tyr Lys Asp Gly Arg Ala Asn Val Leu Val Lys Val Asn Asn
    130                 135                 140

Thr Gln Pro Ser Ser Arg Trp Tyr Ser Gly Ser Gly Ile Tyr Arg Asn
145                 150                 155                 160

Val Tyr Leu Thr Val Thr Asp Pro Ile His Val Ala Arg Tyr Gly Thr
                165                 170                 175

Phe Val Thr Thr Pro Asn Leu Glu Lys Ser Ile Lys Glu Asp Arg Ala
            180                 185                 190

Asp Val Asn Ile Lys Thr Lys Ile Ser Asn Asp Ala Ala Glu Ala Lys
        195                 200                 205

Gln Val Lys Ile Lys Ser Thr Ile Tyr Asp Gly Ala Gly Asn Thr Val
    210                 215                 220

Gln Thr Val Glu Thr Glu Glu Lys Thr Ala Ala Ala Gly Thr Val Thr
225                 230                 235                 240

Pro Phe Glu Gln Asn Thr Val Ile Lys Gln Pro Lys Leu Trp Ser Ile
                245                 250                 255
```

-continued

```
Asp Lys Pro Tyr Arg Tyr Asn Leu Val Thr Glu Val Ile Val Gly Gly
            260                 265                 270
Gln Thr Val Asp Thr Tyr Glu Thr Lys Phe Gly Val Arg Tyr Phe Lys
        275                 280                 285
Phe Asp Glu Asn Glu Gly Phe Ser Leu Asn Gly Glu Tyr Met Lys Leu
    290                 295                 300
His Gly Val Ser Met His His Asp Leu Gly Ala Leu Gly Ala Ala Thr
305                 310                 315                 320
Asn Ala Arg Gly Val Glu Arg Gln Met Gln Ile Met Lys Asp Met Gly
                325                 330                 335
Val Asn Ala Ile Arg Val Thr His Asn Pro Ala Ser Pro Glu Leu Leu
            340                 345                 350
Glu Ala Ala Asn Lys Leu Gly Leu Phe Ile Ile Glu Glu Ala Phe Asp
        355                 360                 365
Ser Trp Ala Gln Ser Lys Lys Pro Tyr Asp Tyr Gly Arg Phe Phe Asn
    370                 375                 380
Ala Trp Ala Glu His Asp Ile Lys Glu Met Val Asp Arg Gly Lys Asn
385                 390                 395                 400
Glu Pro Ala Ile Ile Met Trp Ser Ile Gly Asn Glu Ile Tyr Asp Thr
                405                 410                 415
Thr Asn Ala Ala Gly Val Glu Thr Ala Arg Asn Leu Val Gly Trp Val
            420                 425                 430
Lys Glu Ile Asp Thr Thr Arg Pro Thr Thr Ile Gly Glu Asp Lys Thr
        435                 440                 445
Arg Gly Asp Lys Val Asn Val Thr Pro Ile Asn Ser Tyr Ile Lys Glu
    450                 455                 460
Ile Phe Asn Ile Val Asp Val Val Gly Leu Asn Tyr Ser Glu Asn Asn
465                 470                 475                 480
Tyr Asp Gly Tyr His Lys Gln Asn Pro Ser Trp Lys Leu Tyr Gly Ser
                485                 490                 495
Glu Thr Ser Ser Ala Thr Arg Ser Arg Gly Val Tyr Thr His Pro Tyr
            500                 505                 510
Gln Tyr Asn Gln Ser Thr Lys Tyr Ala Asp Leu Gln Gln Ser Ser Tyr
        515                 520                 525
Asp Asn Asp Tyr Val Gly Trp Gly Arg Thr Ala Glu Asp Ala Trp Lys
    530                 535                 540
Tyr Asp Arg Asp Leu Lys His Ile Ala Gly Gln Phe Ile Trp Thr Gly
545                 550                 555                 560
Phe Asp Tyr Ile Gly Glu Pro Thr Pro Tyr Tyr Asn Ser Tyr Pro Ala
                565                 570                 575
Lys Ser Ser Tyr Phe Gly Ala Val Asp Thr Ala Gly Phe Pro Lys Asp
            580                 585                 590
Ile Phe Tyr Tyr Tyr Gln Ser Gln Trp Lys Lys Glu Pro Met Val His
        595                 600                 605
Leu Leu Pro His Trp Asn Trp Lys Glu Gly Lys Val Arg Val Leu
    610                 615                 620
Ala Tyr Thr Asn Ala Ser Lys Val Glu Leu Val Leu Asn Gly Glu Ser
625                 630                 635                 640
Leu Gly Glu Lys Asn Tyr Asp Asn Lys Gln Thr Ser Trp Gly Ala Pro
                645                 650                 655
Tyr Lys Glu Thr Lys Asp Gly Lys Thr Tyr Leu Glu Trp Ala Val Pro
            660                 665                 670
Phe Lys Pro Gly Lys Leu Glu Ala Val Ala Lys Asp Glu Asn Gly Lys
```

-continued

|     |     |     |     |     | 675 |     |     |     | 680 |     |     |     | 685 |     |
|-----|-----|-----|-----|-----|-----|-----|-----|-----|-----|-----|-----|-----|-----|-----|
| Val | Ile | Ala | Arg | Asp | Gln | Val | Val | Thr | Ala | Gly | Glu | Pro | Ala | Ser | Val |

Val Ile Ala Arg Asp Gln Val Val Thr Ala Gly Glu Pro Ala Ser Val
                675                 680                 685

Arg Leu Thr Ala Asp Arg Lys Val Val Lys Ala Asp Gly Thr Asp Leu
705                 710                 715                 720

Ser Phe Ile Thr Ala Asp Ile Val Asp Ser Lys Gly Ile Val Val Pro
                725                 730                 735

Asp Ala Asp His Leu Ile Thr Phe Asn Val Thr Gly Gln Gly Glu Leu
                740                 745                 750

Ala Gly Val Asp Asn Gly Asn Ala Ser Ser Val Glu Arg Tyr Lys Asp
                755                 760                 765

Asn Lys Arg Lys Ala Phe Ser Gly Lys Ala Leu Ala Ile Val Gln Ser
770                 775                 780

Ser Lys Leu Ser Gly Lys Ile Thr Val His Ala Ser Val Ala Gly Leu
785                 790                 795                 800

Ser Ser Asp Ser Thr Ser Val Phe Thr Val Thr Pro Ala Asp His Asp
                805                 810                 815

Lys Lys Ile Val Ala Gly Ile Asp Asp Val Asn Leu Thr Val Asp Val
                820                 825                 830

Asn Glu Ala Pro Lys Leu Pro Ser Glu Ile Lys Val Tyr Tyr Ser Asp
                835                 840                 845

Glu Ser Ala Ala Ala Lys Asn Val Thr Trp Asp Glu Val Asp Pro Lys
850                 855                 860

Gln Tyr Ser Thr Val Gly Glu Phe Thr Val Glu Gly Ser Val Glu Gly
865                 870                 875                 880

Thr Ser Leu Lys Ala Lys Ala Phe Val Ile Val Lys Gly Ile Val Ala
                885                 890                 895

Val Lys Pro Tyr Ser Thr Ala Thr Lys Val Gly Val Gln Pro Val Leu
                900                 905                 910

Pro Glu Lys Ala Thr Leu Leu Tyr Ser Asp Gly Thr Thr Lys Gly Ala
                915                 920                 925

Thr Val Thr Trp Asp Glu Ile Pro Glu Asp Lys Leu Ala Lys Glu Gly
                930                 935                 940

Arg Phe Thr Val Glu Gly Ser Val Glu Gly Thr Asp Leu Lys Ala Asn
945                 950                 955                 960

Val Tyr Val Arg Val Thr Asn Glu Val Lys Ser Val Asn Ile Met Leu
                965                 970                 975

Gln Glu Gln Gly Ser Ala Tyr Pro Lys Leu Glu Ala Thr Phe Thr Asn
                980                 985                 990

Pro Ala Asp Asn Leu Gln His Leu Asn Asp Gly Ile Lys Ser Tyr Thr
                995                 1000                1005

Asn Asn Pro Val Asn Arg Trp Thr Asn Trp Thr Arg Thr Pro Arg
                1010                1015                1020

Asp Ala Gly Asp Ser Ile Thr Val Asn Phe Gly Lys Lys His Val
                1025                1030                1035

Ile Asn Asn Leu Asp Leu Phe Val Phe Thr Asp Ser Gly Thr Val
                1040                1045                1050

Val Pro Glu Lys Ala Glu Val Gln Tyr Trp Asp Gly Thr Ala Trp
                1055                1060                1065

Lys Asp Val Glu Asn Leu Thr Gln Pro Ser Pro Tyr Val Val Glu
                1070                1075                1080

Lys Asn Glu Leu Thr Phe Asp Ala Val Ala Thr Glu Lys Leu Lys
                1085                1090                1095

-continued

Phe His Leu Thr Pro Ser Val Lys Gly Lys Phe Leu Ala Leu Thr
1100            1105                1110

Glu Ala Glu Val Tyr Ala Asp Gln Ile Val Met Gly Glu Thr Ala
1115            1120                1125

Lys Leu Gln Ser Ile Thr Val Asn Gly Lys Ala Leu Glu Gly Phe
1130            1135                1140

Asp His Ala Lys Lys Asn Tyr Glu Leu Val Leu Pro Tyr Gly Ser
1145            1150                1155

Glu Leu Pro Lys Ile Glu Ala Ala Ala Asp Asn Ala Thr Val
1160            1165                1170

Thr Ile Leu Pro Ala Phe Ser Tyr Pro Gly Thr Ala Lys Leu Phe
1175            1180                1185

Val Thr Ser Glu Asp Gly Lys Val Thr Thr Glu Tyr Ser Ile Gly
1190            1195                1200

Val Ser Thr Glu Glu Pro Lys Leu Val Ser Ala Glu Leu Ser Ala
1205            1210                1215

Asp Lys Thr Asn Val Met Glu Asp Asp Ile Ile Asp Leu Lys Val
1220            1225                1230

Ile Gly Leu Phe Glu Ser Lys Glu Lys Ile Asp Val Thr Asp Ser
1235            1240                1245

Gln Pro Thr Tyr Glu Phe Asp Gln Gln Ile Ile Lys Ile Glu Gly
1250            1255                1260

Asn Lys Leu Tyr Ala Leu Glu Thr Gly Asn Val Lys Val Lys Val
1265            1270                1275

Thr Val Thr Tyr Lys Gly Val Ser Val Thr Thr Pro Ala Leu Glu
1280            1285                1290

Phe Thr Ile Ala Lys Asn Pro Ala Pro Lys Tyr Ile Thr Ser Leu
1295            1300                1305

Glu Pro Val Thr Val Val Lys Lys Gly Glu Ala Pro Glu Leu
1310            1315                1320

Pro Ala Thr Val Val Ala His Tyr Asn Arg Gly Ile Pro Arg Asp
1325            1330                1335

Val Lys Val Lys Trp Glu Arg Ile Asn Pro Ser Lys Tyr Gln Gln
1340            1345                1350

Leu Gly Glu Phe Thr Val Ser Gly Met Val Glu Gly Thr Asp Ile
1355            1360                1365

Lys Ala Gln Ala Lys Val Ile Val Lys Gly Ala Val Ala Val Glu
1370            1375                1380

Asp Ile Arg Met Ala Val Leu Leu Lys Gln Met Pro Gln Leu Pro
1385            1390                1395

Gly Lys Val Thr Val Tyr Tyr Ser Asp Gly Ala Glu Glu Gln Arg
1400            1405                1410

Ala Val Lys Trp Glu Glu Ile Pro Gln Glu Glu Leu Glu Asn Val
1415            1420                1425

Gly Glu Phe Lys Val Lys Gly Asp Val Asn Gly Val Lys Leu Lys
1430            1435                1440

Ala Thr Ala Thr Ile Arg Val Thr Asp Glu Val Gly Gly Glu Gln
1445            1450                1455

Asn Ile Ser Arg Ala Lys Asn Gly Tyr Glu Tyr Pro Lys Ala Glu
1460            1465                1470

Ala Ser Phe Thr Asn Asn Gly Pro Gly Ser Ser Asp Arg Ile Glu
1475            1480                1485

```
Ala Ile Asn Asp Asp Val Ile Ser Tyr Glu Ala Asn Pro His Asn
    1490                1495                1500

Arg Trp Thr Asn Trp Gln Pro Val Pro Arg Ala Gly Asp Trp Val
1505                1510                1515

Ser Ile Thr Phe Gly Asp Tyr Glu Pro Thr Glu Tyr Asp Val Asp
1520                1525                1530

Ser Met Glu Ile His Trp Phe Ala Asp His Gly Thr Ser Tyr Pro
1535                1540                1545

Glu Arg Phe Gln Ile Glu Tyr Lys Ser Gly Asp Ser Trp Lys Glu
1550                1555                1560

Val Thr Ser Leu Lys Ser Asp Pro Ala Ser Pro Ala Leu Gly Lys
1565                1570                1575

Ala Asn Val Tyr Ser Phe Asp Arg Val Lys Thr Ser Ala Ile Arg
1580                1585                1590

Val Lys Met Thr Ala Gln Ala Gly Lys Ser Leu Ala Ile Thr Glu
1595                1600                1605

Leu Lys Val Phe Ser Lys Trp Pro Lys Ala Gly Thr Glu Pro Glu
1610                1615                1620

Val Thr Asp Ile Lys Val Gly Gly Lys Ser Ile Leu Glu Asp Phe
1625                1630                1635

Glu Gln Lys Gly Asp His Tyr Glu Val Thr Ile Asp Ala Gly Asp
1640                1645                1650

Ala Asn Val Met Pro Lys Ile Asn Val Lys Ala Lys Asp Gln Thr
1655                1660                1665

Ser Ile Thr Ile Val Pro Ala Val Thr Ser Pro Ser Thr Ala Lys
1670                1675                1680

Val Ile Ala Lys Ser Glu Asp Gly Lys Lys Val Lys Val Tyr Ser
1685                1690                1695

Ile His Tyr Lys
1700

<210> SEQ ID NO 8
<211> LENGTH: 1214
<212> TYPE: PRT
<213> ORGANISM: Bacillus circulans

<400> SEQUENCE: 8

Gly Asn Ser Val Ser Tyr Asp Gly Glu Arg Arg Val Asn Phe Asn Glu
1               5                   10                  15

Asn Trp Arg Phe Gln Arg Glu Thr Asn Gly Ser Ile Ala Gly Ala Gln
                20                  25                  30

Asn Pro Gly Phe Asp Asp Ser Ser Trp Arg Lys Leu Asn Leu Pro His
            35                  40                  45

Asp Trp Ser Ile Glu Leu Asp Phe Asn Lys Asn Ser Leu Ala Thr His
        50                  55                  60

Glu Gly Gly Tyr Leu Asp Gly Ile Gly Trp Tyr Arg Lys Thr Phe
65                  70                  75                  80

Thr Ile Pro Glu Ser Met Lys Gly Lys Arg Ile Ser Leu Asp Phe Asp
                85                  90                  95

Gly Val Tyr Met Asn Ser Thr Thr Tyr Leu Asn Gly Glu Val Leu Gly
            100                 105                 110

Thr Tyr Pro Phe Gly Tyr Asn Ala Phe Ser Tyr Asp Ile Ser Asp Lys
        115                 120                 125

Leu Tyr Lys Asp Gly Arg Ala Asn Val Leu Val Val Lys Val Asn Asn
    130                 135                 140
```

```
Thr Gln Pro Ser Ser Arg Trp Tyr Ser Gly Ser Gly Ile Tyr Arg Asn
145                 150                 155                 160

Val Tyr Leu Thr Val Thr Asp Pro Ile His Val Ala Arg Tyr Gly Thr
            165                 170                 175

Phe Val Thr Thr Pro Asn Leu Glu Lys Ser Ile Lys Glu Asp Arg Ala
        180                 185                 190

Asp Val Asn Ile Lys Thr Lys Ile Ser Asn Asp Ala Ala Glu Ala Lys
    195                 200                 205

Gln Val Lys Ile Lys Ser Thr Ile Tyr Asp Gly Ala Gly Asn Thr Val
210                 215                 220

Gln Thr Val Glu Thr Glu Lys Thr Ala Ala Gly Thr Val Thr
225                 230                 235                 240

Pro Phe Glu Gln Asn Thr Val Ile Lys Gln Pro Lys Leu Trp Ser Ile
                245                 250                 255

Asp Lys Pro Tyr Arg Tyr Asn Leu Val Thr Glu Val Ile Val Gly Gly
            260                 265                 270

Gln Thr Val Asp Thr Tyr Glu Thr Lys Phe Gly Val Arg Tyr Phe Lys
        275                 280                 285

Phe Asp Glu Asn Glu Gly Phe Ser Leu Asn Gly Glu Tyr Met Lys Leu
    290                 295                 300

His Gly Val Ser Met His His Asp Leu Gly Ala Leu Gly Ala Ala Thr
305                 310                 315                 320

Asn Ala Arg Gly Val Glu Arg Gln Met Gln Ile Met Lys Asp Met Gly
                325                 330                 335

Val Asn Ala Ile Arg Val Thr His Asn Pro Ala Ser Pro Glu Leu Leu
            340                 345                 350

Glu Ala Ala Asn Lys Leu Gly Leu Phe Ile Ile Glu Glu Ala Phe Asp
        355                 360                 365

Ser Trp Ala Gln Ser Lys Lys Pro Tyr Asp Tyr Gly Arg Phe Phe Asn
    370                 375                 380

Ala Trp Ala Glu His Asp Ile Lys Glu Met Val Asp Arg Gly Lys Asn
385                 390                 395                 400

Glu Pro Ala Ile Ile Met Trp Ser Ile Gly Asn Glu Ile Tyr Asp Thr
                405                 410                 415

Thr Asn Ala Ala Gly Val Glu Thr Ala Arg Asn Leu Val Gly Trp Val
            420                 425                 430

Lys Glu Ile Asp Thr Thr Arg Pro Thr Thr Ile Gly Glu Asp Lys Thr
        435                 440                 445

Arg Gly Asp Lys Val Asn Val Thr Pro Ile Asn Ser Tyr Ile Lys Glu
450                 455                 460

Ile Phe Asn Ile Val Asp Val Val Gly Leu Asn Tyr Ser Glu Asn Asn
465                 470                 475                 480

Tyr Asp Gly Tyr His Lys Gln Asn Pro Ser Trp Lys Leu Tyr Gly Ser
                485                 490                 495

Glu Thr Ser Ser Ala Thr Arg Ser Arg Gly Val Tyr Thr His Pro Tyr
            500                 505                 510

Gln Tyr Asn Gln Ser Thr Lys Tyr Ala Asp Leu Gln Gln Ser Ser Tyr
        515                 520                 525

Asp Asn Asp Tyr Val Gly Trp Gly Arg Thr Ala Glu Asp Ala Trp Lys
    530                 535                 540

Tyr Asp Arg Asp Leu Lys His Ile Ala Gly Gln Phe Ile Trp Thr Gly
545                 550                 555                 560
```

```
Phe Asp Tyr Ile Gly Glu Pro Thr Pro Tyr Asn Ser Tyr Pro Ala
            565                 570                 575
Lys Ser Ser Tyr Phe Gly Ala Val Asp Thr Ala Gly Phe Pro Lys Asp
        580                 585                 590
Ile Phe Tyr Tyr Tyr Gln Ser Gln Trp Lys Lys Glu Pro Met Val His
            595                 600                 605
Leu Leu Pro His Trp Asn Trp Lys Glu Gly Glu Lys Val Arg Val Leu
        610                 615                 620
Ala Tyr Thr Asn Ala Ser Lys Val Glu Leu Val Leu Asn Gly Glu Ser
625                 630                 635                 640
Leu Gly Glu Lys Asn Tyr Asp Asn Lys Gln Thr Ser Trp Gly Ala Pro
            645                 650                 655
Tyr Lys Glu Thr Lys Asp Gly Lys Thr Tyr Leu Glu Trp Ala Val Pro
            660                 665                 670
Phe Lys Pro Gly Lys Leu Glu Ala Val Ala Lys Asp Glu Asn Gly Lys
        675                 680                 685
Val Ile Ala Arg Asp Gln Val Val Thr Ala Gly Glu Pro Ala Ser Val
        690                 695                 700
Arg Leu Thr Ala Asp Arg Lys Val Val Lys Ala Asp Gly Thr Asp Leu
705                 710                 715                 720
Ser Phe Ile Thr Ala Asp Ile Val Asp Ser Lys Gly Ile Val Val Pro
            725                 730                 735
Asp Ala Asp His Leu Ile Thr Phe Asn Val Thr Gly Gln Gly Glu Leu
            740                 745                 750
Ala Gly Val Asp Asn Gly Asn Ala Ser Ser Val Glu Arg Tyr Lys Asp
        755                 760                 765
Asn Lys Arg Lys Ala Phe Ser Gly Lys Ala Leu Ala Ile Val Gln Ser
        770                 775                 780
Ser Lys Leu Ser Gly Lys Ile Thr Val His Ala Ser Val Ala Gly Leu
785                 790                 795                 800
Ser Ser Asp Ser Thr Ser Val Phe Thr Val Thr Pro Ala Asp His Asp
            805                 810                 815
Lys Lys Ile Val Ala Gly Ile Asp Asp Val Asn Leu Thr Val Asp Val
        820                 825                 830
Asn Glu Ala Pro Lys Leu Pro Ser Glu Ile Lys Val Tyr Tyr Ser Asp
        835                 840                 845
Glu Ser Ala Ala Lys Asn Val Thr Trp Asp Glu Val Asp Pro Lys
850                 855                 860
Gln Tyr Ser Thr Val Gly Glu Phe Thr Val Glu Gly Ser Val Glu Gly
865                 870                 875                 880
Thr Ser Leu Lys Ala Lys Ala Phe Val Ile Val Lys Gly Ile Val Ala
            885                 890                 895
Val Lys Pro Tyr Ser Thr Ala Thr Lys Val Gly Val Gln Pro Val Leu
        900                 905                 910
Pro Glu Lys Ala Thr Leu Leu Tyr Ser Asp Gly Thr Thr Lys Gly Ala
            915                 920                 925
Thr Val Thr Trp Asp Glu Ile Pro Glu Asp Lys Leu Ala Lys Glu Gly
        930                 935                 940
Arg Phe Thr Val Glu Gly Ser Val Glu Gly Thr Asp Leu Lys Ala Asn
945                 950                 955                 960
Val Tyr Val Arg Val Thr Asn Glu Val Lys Ser Val Asn Ile Met Leu
            965                 970                 975
Gln Glu Gln Gly Ser Ala Tyr Pro Lys Leu Glu Ala Thr Phe Thr Asn
```

```
Pro Ala Asp Asn Leu Gln His Leu Asn Asp Gly Ile Lys Ser Tyr Thr
            980                 985                 990
                995                1000                1005

Asn Asn Pro Val Asn Arg Trp Thr Asn Trp Thr Arg Thr Pro Arg
    1010                1015                1020

Asp Ala Gly Asp Ser Ile Thr Val Asn Phe Gly Lys Lys His Val
    1025                1030                1035

Ile Asn Asn Leu Asp Leu Phe Val Phe Thr Asp Ser Gly Thr Val
    1040                1045                1050

Val Pro Glu Lys Ala Glu Val Gln Tyr Trp Asp Gly Thr Ala Trp
    1055                1060                1065

Lys Asp Val Glu Asn Leu Thr Gln Pro Ser Pro Tyr Val Val Glu
    1070                1075                1080

Lys Asn Glu Leu Thr Phe Asp Ala Val Ala Thr Glu Lys Leu Lys
    1085                1090                1095

Phe His Leu Thr Pro Ser Val Lys Gly Lys Phe Leu Ala Leu Thr
    1100                1105                1110

Glu Ala Glu Val Tyr Ala Asp Gln Ile Val Met Gly Glu Thr Ala
    1115                1120                1125

Lys Leu Gln Ser Ile Thr Val Asn Gly Lys Ala Leu Glu Gly Phe
    1130                1135                1140

Asp His Ala Lys Lys Asn Tyr Glu Leu Val Leu Pro Tyr Gly Ser
    1145                1150                1155

Glu Leu Pro Lys Ile Glu Ala Ala Ala Asp Asn Ala Thr Val
    1160                1165                1170

Thr Ile Leu Pro Ala Phe Ser Tyr Pro Gly Thr Ala Lys Leu Phe
    1175                1180                1185

Val Thr Ser Glu Asp Gly Lys Val Thr Thr Glu Tyr Ser Ile Gly
    1190                1195                1200

Val Ser Thr Glu Glu Pro Lys Leu Val Ser Ala
    1205                1210

<210> SEQ ID NO 9
<211> LENGTH: 812
<212> TYPE: PRT
<213> ORGANISM: Bacillus circulans

<400> SEQUENCE: 9

Gly Asn Ser Val Ser Tyr Asp Gly Glu Arg Arg Val Asn Phe Asn Glu
1               5                   10                  15

Asn Trp Arg Phe Gln Arg Glu Thr Asn Gly Ser Ile Ala Gly Ala Gln
                20                  25                  30

Asn Pro Gly Phe Asp Asp Ser Ser Trp Arg Lys Leu Asn Leu Pro His
            35                  40                  45

Asp Trp Ser Ile Glu Leu Asp Phe Asn Lys Asn Ser Leu Ala Thr His
        50                  55                  60

Glu Gly Gly Tyr Leu Asp Gly Gly Ile Gly Trp Tyr Arg Lys Thr Phe
65                  70                  75                  80

Thr Ile Pro Glu Ser Met Lys Gly Lys Arg Ile Ser Leu Asp Phe Asp
                85                  90                  95

Gly Val Tyr Met Asn Ser Thr Thr Tyr Leu Asn Gly Glu Val Leu Gly
            100                 105                 110

Thr Tyr Pro Phe Gly Tyr Asn Ala Phe Ser Tyr Asp Ile Ser Asp Lys
        115                 120                 125
```

```
Leu Tyr Lys Asp Gly Arg Ala Asn Val Leu Val Lys Val Asn Asn
    130                 135                 140

Thr Gln Pro Ser Ser Arg Trp Tyr Ser Gly Gly Ile Tyr Arg Asn
145                 150                 155                 160

Val Tyr Leu Thr Val Thr Asp Pro Ile His Val Ala Arg Tyr Gly Thr
                165                 170                 175

Phe Val Thr Thr Pro Asn Leu Glu Lys Ser Ile Lys Glu Asp Arg Ala
            180                 185                 190

Asp Val Asn Ile Lys Thr Lys Ile Ser Asn Asp Ala Ala Glu Ala Lys
            195                 200                 205

Gln Val Lys Ile Lys Ser Thr Ile Tyr Asp Gly Ala Gly Asn Thr Val
    210                 215                 220

Gln Thr Val Glu Thr Glu Lys Thr Ala Ala Ala Gly Thr Val Thr
225                 230                 235                 240

Pro Phe Glu Gln Asn Thr Val Ile Lys Gln Pro Lys Leu Trp Ser Ile
                245                 250                 255

Asp Lys Pro Tyr Arg Tyr Asn Leu Val Thr Glu Val Ile Val Gly Gly
            260                 265                 270

Gln Thr Val Asp Thr Tyr Glu Thr Lys Phe Gly Val Arg Tyr Phe Lys
            275                 280                 285

Phe Asp Glu Asn Glu Gly Phe Ser Leu Asn Gly Glu Tyr Met Lys Leu
    290                 295                 300

His Gly Val Ser Met His His Asp Leu Gly Ala Leu Gly Ala Ala Thr
305                 310                 315                 320

Asn Ala Arg Gly Val Glu Arg Gln Met Gln Ile Met Lys Asp Met Gly
                325                 330                 335

Val Asn Ala Ile Arg Val Thr His Asn Pro Ala Ser Pro Glu Leu Leu
            340                 345                 350

Glu Ala Ala Asn Lys Leu Gly Leu Phe Ile Ile Glu Glu Ala Phe Asp
    355                 360                 365

Ser Trp Ala Gln Ser Lys Lys Pro Tyr Asp Tyr Gly Arg Phe Phe Asn
370                 375                 380

Ala Trp Ala Glu His Asp Ile Lys Glu Met Val Asp Arg Gly Lys Asn
385                 390                 395                 400

Glu Pro Ala Ile Ile Met Trp Ser Ile Gly Asn Glu Ile Tyr Asp Thr
                405                 410                 415

Thr Asn Ala Ala Gly Val Glu Thr Ala Arg Asn Leu Val Gly Trp Val
            420                 425                 430

Lys Glu Ile Asp Thr Thr Arg Pro Thr Thr Ile Gly Glu Asp Lys Thr
            435                 440                 445

Arg Gly Asp Lys Val Asn Val Thr Pro Ile Asn Ser Tyr Ile Lys Glu
    450                 455                 460

Ile Phe Asn Ile Val Asp Val Val Gly Leu Asn Tyr Ser Glu Asn Asn
465                 470                 475                 480

Tyr Asp Gly Tyr His Lys Gln Asn Pro Ser Trp Lys Leu Tyr Gly Ser
                485                 490                 495

Glu Thr Ser Ser Ala Thr Arg Ser Arg Gly Val Tyr Thr His Pro Tyr
            500                 505                 510

Gln Tyr Asn Gln Ser Thr Lys Tyr Ala Asp Leu Gln Gln Ser Ser Tyr
            515                 520                 525

Asp Asn Asp Tyr Val Gly Trp Gly Arg Thr Ala Glu Asp Ala Trp Lys
    530                 535                 540

Tyr Asp Arg Asp Leu Lys His Ile Ala Gly Gln Phe Ile Trp Thr Gly
```

```
                545                 550                 555                 560
        Phe Asp Tyr Ile Gly Glu Pro Thr Pro Tyr Tyr Asn Ser Tyr Pro Ala
                        565                 570                 575

Lys Ser Ser Tyr Phe Gly Ala Val Asp Thr Ala Gly Phe Pro Lys Asp
                        580                 585                 590

Ile Phe Tyr Tyr Tyr Gln Ser Gln Trp Lys Lys Glu Pro Met Val His
                        595                 600                 605

Leu Leu Pro His Trp Asn Trp Lys Glu Gly Lys Val Arg Val Leu
                610                 615                 620

Ala Tyr Thr Asn Ala Ser Lys Val Glu Leu Val Leu Asn Gly Glu Ser
        625                 630                 635                 640

Leu Gly Glu Lys Asn Tyr Asp Asn Lys Gln Thr Ser Trp Gly Ala Pro
                        645                 650                 655

Tyr Lys Glu Thr Lys Asp Gly Lys Thr Tyr Leu Glu Trp Ala Val Pro
                        660                 665                 670

Phe Lys Pro Gly Lys Leu Glu Ala Val Ala Lys Asp Glu Asn Gly Lys
                        675                 680                 685

Val Ile Ala Arg Asp Gln Val Val Thr Ala Gly Glu Pro Ala Ser Val
                690                 695                 700

Arg Leu Thr Ala Asp Arg Lys Val Val Lys Ala Asp Gly Thr Asp Leu
        705                 710                 715                 720

Ser Phe Ile Thr Ala Asp Ile Val Asp Ser Lys Gly Ile Val Val Pro
                        725                 730                 735

Asp Ala Asp His Leu Ile Thr Phe Asn Val Thr Gly Gln Gly Glu Leu
                        740                 745                 750

Ala Gly Val Asp Asn Gly Asn Ala Ser Ser Val Glu Arg Tyr Lys Asp
                        755                 760                 765

Asn Lys Arg Lys Ala Phe Ser Gly Lys Ala Leu Ala Ile Val Gln Ser
                        770                 775                 780

Ser Lys Leu Ser Gly Lys Ile Thr Val His Ala Ser Val Ala Gly Leu
        785                 790                 795                 800

Ser Ser Asp Ser Thr Ser Val Phe Thr Val Thr Pro
                        805                 810

<210> SEQ ID NO 10
<211> LENGTH: 1387
<212> TYPE: PRT
<213> ORGANISM: Bacillus circulans

<400> SEQUENCE: 10

Gly Asn Ser Val Ser Tyr Asp Gly Glu Arg Arg Val Asn Phe Asn Glu
1               5                   10                  15

Asn Trp Arg Phe Gln Arg Glu Thr Asn Gly Ser Ile Ala Gly Ala Gln
                20                  25                  30

Asn Pro Gly Phe Asp Asp Ser Ser Trp Arg Lys Leu Asn Leu Pro His
                35                  40                  45

Asp Trp Ser Ile Glu Leu Asp Phe Asn Lys Asn Ser Leu Ala Thr His
        50                  55                  60

Glu Gly Gly Tyr Leu Asp Gly Ile Gly Trp Tyr Arg Lys Thr Phe
65                  70                  75                  80

Thr Ile Pro Glu Ser Met Lys Gly Lys Arg Ile Ser Leu Asp Phe Asp
                85                  90                  95

Gly Val Tyr Met Asn Ser Thr Thr Tyr Leu Asn Gly Glu Val Leu Gly
                100                 105                 110
```

-continued

```
Thr Tyr Pro Phe Gly Tyr Asn Ala Phe Ser Tyr Asp Ile Ser Asp Lys
        115                 120                 125
Leu Tyr Lys Asp Gly Arg Ala Asn Val Leu Val Val Lys Val Asn Asn
130                 135                 140
Thr Gln Pro Ser Ser Arg Trp Tyr Ser Gly Gly Ile Tyr Arg Asn
145                 150                 155                 160
Val Tyr Leu Thr Val Thr Asp Pro Ile His Val Ala Arg Tyr Gly Thr
                    165                 170                 175
Phe Val Thr Thr Pro Asn Leu Glu Lys Ser Ile Lys Glu Asp Arg Ala
                180                 185                 190
Asp Val Asn Ile Lys Thr Lys Ile Ser Asn Asp Ala Ala Glu Ala Lys
            195                 200                 205
Gln Val Lys Ile Lys Ser Thr Ile Tyr Asp Gly Ala Gly Asn Thr Val
210                 215                 220
Gln Thr Val Glu Thr Glu Lys Thr Ala Ala Gly Thr Val Thr
225                 230                 235                 240
Pro Phe Glu Gln Asn Thr Val Ile Lys Gln Pro Lys Leu Trp Ser Ile
                245                 250                 255
Asp Lys Pro Tyr Arg Tyr Asn Leu Val Thr Glu Val Ile Val Gly Gly
            260                 265                 270
Gln Thr Val Asp Thr Tyr Glu Thr Lys Phe Gly Val Arg Tyr Phe Lys
    275                 280                 285
Phe Asp Glu Asn Glu Gly Phe Ser Leu Asn Gly Glu Tyr Met Lys Leu
    290                 295                 300
His Gly Val Ser Met His His Asp Leu Gly Ala Leu Gly Ala Ala Thr
305                 310                 315                 320
Asn Ala Arg Gly Val Glu Arg Gln Met Gln Ile Met Lys Asp Met Gly
                325                 330                 335
Val Asn Ala Ile Arg Val Thr His Asn Pro Ala Ser Pro Glu Leu Leu
                340                 345                 350
Glu Ala Ala Asn Lys Leu Gly Leu Phe Ile Ile Glu Glu Ala Phe Asp
            355                 360                 365
Ser Trp Ala Gln Ser Lys Lys Pro Tyr Asp Tyr Gly Arg Phe Phe Asn
370                 375                 380
Ala Trp Ala Glu His Asp Ile Lys Glu Met Val Asp Arg Gly Lys Asn
385                 390                 395                 400
Glu Pro Ala Ile Ile Met Trp Ser Ile Gly Asn Glu Ile Tyr Asp Thr
                405                 410                 415
Thr Asn Ala Ala Gly Val Glu Thr Ala Arg Asn Leu Val Gly Trp Val
            420                 425                 430
Lys Glu Ile Asp Thr Thr Arg Pro Thr Thr Ile Gly Glu Asp Lys Thr
        435                 440                 445
Arg Gly Asp Lys Val Asn Val Thr Pro Ile Asn Ser Tyr Ile Lys Glu
    450                 455                 460
Ile Phe Asn Ile Val Asp Val Val Gly Leu Asn Tyr Ser Glu Asn Asn
465                 470                 475                 480
Tyr Asp Gly Tyr His Lys Gln Asn Pro Ser Trp Lys Leu Tyr Gly Ser
                485                 490                 495
Glu Thr Ser Ser Ala Thr Arg Ser Arg Gly Val Tyr Thr His Pro Tyr
            500                 505                 510
Gln Tyr Asn Gln Ser Thr Lys Tyr Ala Asp Leu Gln Gln Ser Ser Tyr
        515                 520                 525
Asp Asn Asp Tyr Val Gly Trp Gly Arg Thr Ala Glu Asp Ala Trp Lys
```

```
                530                 535                 540
Tyr Asp Arg Asp Leu Lys His Ile Ala Gly Gln Phe Ile Trp Thr Gly
545                 550                 555                 560

Phe Asp Tyr Ile Gly Glu Pro Thr Pro Tyr Tyr Asn Ser Tyr Pro Ala
                565                 570                 575

Lys Ser Ser Tyr Phe Gly Ala Val Asp Thr Ala Gly Phe Pro Lys Asp
                580                 585                 590

Ile Phe Tyr Tyr Gln Ser Gln Trp Lys Lys Glu Pro Met Val His
                595                 600                 605

Leu Leu Pro His Trp Asn Trp Lys Glu Gly Glu Lys Val Arg Val Leu
                610                 615                 620

Ala Tyr Thr Asn Ala Ser Lys Val Glu Leu Val Leu Asn Gly Glu Ser
625                 630                 635                 640

Leu Gly Glu Lys Asn Tyr Asp Asn Lys Gln Thr Ser Trp Gly Ala Pro
                645                 650                 655

Tyr Lys Glu Thr Lys Asp Gly Lys Thr Tyr Leu Glu Trp Ala Val Pro
                660                 665                 670

Phe Lys Pro Gly Lys Leu Glu Ala Val Ala Lys Asp Glu Asn Gly Lys
                675                 680                 685

Val Ile Ala Arg Asp Gln Val Val Thr Ala Gly Glu Pro Ala Ser Val
                690                 695                 700

Arg Leu Thr Ala Asp Arg Lys Val Val Lys Ala Asp Gly Thr Asp Leu
705                 710                 715                 720

Ser Phe Ile Thr Ala Asp Ile Val Asp Ser Lys Gly Ile Val Val Pro
                725                 730                 735

Asp Ala Asp His Leu Ile Thr Phe Asn Val Thr Gly Gln Gly Glu Leu
                740                 745                 750

Ala Gly Val Asp Asn Gly Asn Ala Ser Ser Val Glu Arg Tyr Lys Asp
                755                 760                 765

Asn Lys Arg Lys Ala Phe Ser Gly Lys Ala Leu Ala Ile Val Gln Ser
                770                 775                 780

Ser Lys Leu Ser Gly Lys Ile Thr Val His Ala Ser Val Ala Gly Leu
785                 790                 795                 800

Ser Ser Asp Ser Thr Ser Val Phe Thr Val Thr Pro Ala Asp His Asp
                805                 810                 815

Lys Lys Ile Val Ala Gly Ile Asp Asp Val Asn Leu Thr Val Asp Val
                820                 825                 830

Asn Glu Ala Pro Lys Leu Pro Ser Glu Ile Lys Val Tyr Tyr Ser Asp
                835                 840                 845

Glu Ser Ala Ala Ala Lys Asn Val Thr Trp Asp Glu Val Asp Pro Lys
850                 855                 860

Gln Tyr Ser Thr Val Gly Glu Phe Thr Val Glu Gly Ser Val Glu Gly
865                 870                 875                 880

Thr Ser Leu Lys Ala Lys Ala Phe Val Ile Val Lys Gly Ile Val Ala
                885                 890                 895

Val Lys Pro Tyr Ser Thr Ala Thr Lys Val Gly Val Gln Pro Val Leu
                900                 905                 910

Pro Glu Lys Ala Thr Leu Leu Tyr Ser Asp Gly Thr Thr Lys Gly Ala
                915                 920                 925

Thr Val Thr Trp Asp Glu Ile Pro Glu Asp Lys Leu Ala Lys Glu Gly
                930                 935                 940

Arg Phe Thr Val Glu Gly Ser Val Glu Gly Thr Asp Leu Lys Ala Asn
945                 950                 955                 960
```

-continued

```
Val Tyr Val Arg Val Thr Asn Glu Val Lys Ser Val Asn Ile Met Leu
            965                 970                 975

Gln Glu Gln Gly Ser Ala Tyr Pro Lys Leu Glu Ala Thr Phe Thr Asn
            980                 985                 990

Pro Ala Asp Asn Leu Gln His Leu Asn Asp Gly Ile Lys Ser Tyr Thr
            995                 1000                1005

Asn Asn Pro Val Asn Arg Trp Thr Asn Trp Thr Arg Thr Pro Arg
        1010                1015                1020

Asp Ala Gly Asp Ser Ile Thr Val Asn Phe Gly Lys Lys His Val
        1025                1030                1035

Ile Asn Asn Leu Asp Leu Phe Val Phe Thr Asp Ser Gly Thr Val
        1040                1045                1050

Val Pro Glu Lys Ala Glu Val Gln Tyr Trp Asp Gly Thr Ala Trp
        1055                1060                1065

Lys Asp Val Glu Asn Leu Thr Gln Pro Ser Pro Tyr Val Val Glu
        1070                1075                1080

Lys Asn Glu Leu Thr Phe Asp Ala Val Ala Thr Glu Lys Leu Lys
        1085                1090                1095

Phe His Leu Thr Pro Ser Val Lys Gly Lys Phe Leu Ala Leu Thr
        1100                1105                1110

Glu Ala Glu Val Tyr Ala Asp Gln Ile Val Met Gly Glu Thr Ala
        1115                1120                1125

Lys Leu Gln Ser Ile Thr Val Asn Gly Lys Ala Leu Glu Gly Phe
        1130                1135                1140

Asp His Ala Lys Lys Asn Tyr Glu Leu Val Leu Pro Tyr Gly Ser
        1145                1150                1155

Glu Leu Pro Lys Ile Glu Ala Ala Ala Asp Asn Ala Thr Val
        1160                1165                1170

Thr Ile Leu Pro Ala Phe Ser Tyr Pro Gly Thr Ala Lys Leu Phe
        1175                1180                1185

Val Thr Ser Glu Asp Gly Lys Val Thr Thr Glu Tyr Ser Ile Gly
        1190                1195                1200

Val Ser Thr Glu Glu Pro Lys Leu Val Ser Ala Glu Leu Ser Ala
        1205                1210                1215

Asp Lys Thr Asn Val Met Glu Asp Asp Ile Ile Asp Leu Lys Val
        1220                1225                1230

Ile Gly Leu Phe Glu Ser Lys Glu Lys Ile Asp Val Thr Asp Ser
        1235                1240                1245

Gln Pro Thr Tyr Glu Phe Asp Gln Gln Ile Ile Lys Ile Glu Gly
        1250                1255                1260

Asn Lys Leu Tyr Ala Leu Glu Thr Gly Asn Val Lys Val Lys Val
        1265                1270                1275

Thr Val Thr Tyr Lys Gly Val Ser Val Thr Thr Pro Ala Leu Glu
        1280                1285                1290

Phe Thr Ile Ala Lys Asn Pro Ala Pro Lys Tyr Ile Thr Ser Leu
        1295                1300                1305

Glu Pro Val Thr Val Val Lys Lys Gly Glu Ala Pro Glu Leu
        1310                1315                1320

Pro Ala Thr Val Val Ala His Tyr Asn Arg Gly Ile Pro Arg Asp
        1325                1330                1335

Val Lys Val Lys Trp Glu Arg Ile Asn Pro Ser Lys Tyr Gln Gln
        1340                1345                1350
```

Leu Gly Glu Phe Thr Val Ser Gly Met Val Glu Gly Thr Asp Ile
    1355                1360                1365

Lys Ala Gln Ala Lys Val Ile Val Lys Gly Ala Val Ala Val Glu
1370                1375                1380

Asp Ile Arg Met
    1385

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
aaggtgagct cggaaacagt gtgagc                                          26

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
aaggtgtcga cttatttata gtgaatg                                         27

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
accttgtcga ctcatgcgga gacgagc                                         27

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
accttgtcga ctcacattct aatatcc                                         27

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
catcgcatat gggaaacagt gtgagctatg                                      30

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16

```
tttgtctcta gattatggcg ttaccgtaaa tacg                                    34
```

<210> SEQ ID NO 17
<211> LENGTH: 15
<212> TYPE: PRT
<213> ORGANISM: Bacillus circulans

<400> SEQUENCE: 17

Ser Val Ser Tyr Asp Gly Glu Arg Arg Val Asn Phe Asn Glu Asn
1               5                  10                  15

<210> SEQ ID NO 18
<211> LENGTH: 8
<212> TYPE: PRT
<213> ORGANISM: Bacillus circulans

<400> SEQUENCE: 18

Trp Ser Ile Gly Asn Glu Ile Tyr
1               5